US012697185B2

(12) United States Patent
Lu et al.

(10) Patent No.: US 12,697,185 B2
(45) Date of Patent: Aug. 4, 2026

(54) ROBOT AND MASTER MANIPULATOR THEREOF

(71) Applicant: WUHAN UNITED IMAGING SURGICAL CO., LTD., Wuhan (CN)

(72) Inventors: Zhuangzhuang Lu, Wuhan (CN); Mingchun Zhai, Wuhan (CN); Meng Qu, Wuhan (CN); Wei Jiao, Wuhan (CN)

(73) Assignee: WUHAN UNITED IMAGING SURGICAL CO., LTD., Wuhan (CN)

( * ) Notice: Subject to any disclaimer, the term of this patent is extended or adjusted under 35 U.S.C. 154(b) by 308 days.

(21) Appl. No.: 18/363,689

(22) Filed: Aug. 1, 2023

(65) Prior Publication Data

US 2023/0372043 A1 Nov. 23, 2023

Related U.S. Application Data

(63) Continuation of application No. PCT/CN2022/075244, filed on Jan. 30, 2022.

(30) Foreign Application Priority Data

Feb. 1, 2021 (CN) .......................... 202110135533.0
Apr. 26, 2021 (CN) ......................... 202110454129.X

(51) Int. Cl.
| | |
|---|---|
| *G06F 18/00* | (2023.01) |
| *A61B 34/00* | (2016.01) |
| *B25J 13/06* | (2006.01) |

(52) U.S. Cl.
CPC .............. *A61B 34/71* (2016.02); *A61B 34/76* (2016.02); *B25J 13/065* (2013.01)

(58) Field of Classification Search
CPC ... A61B 2034/742; A61B 34/37; A61B 34/71; A61B 34/74; A61B 34/76; B25J 13/025;
(Continued)

(56) References Cited

U.S. PATENT DOCUMENTS

| | | |
|---|---|---|
| 4,732,353 A | 3/1988 | Studer |
| 6,377,011 B1 | 4/2002 | Ben-Ur |

(Continued)

FOREIGN PATENT DOCUMENTS

| | | |
|---|---|---|
| CN | 101261781 A | 9/2008 |
| CN | 101933837 A | 1/2011 |

(Continued)

OTHER PUBLICATIONS

International Search Report in PCT/CN2022/075244 mailed on Apr. 14, 2022, 7 pages.
(Continued)

*Primary Examiner* — Insa Sadio
(74) *Attorney, Agent, or Firm* — Poseidon Advanced IP LLC

(57) ABSTRACT

Embodiments of the present disclosure provide a robot and a master manipulator thereof. The master manipulator includes: an end control assembly; and an attitude adjustment assembly. The attitude adjustment assembly may include a first mechanism and a second mechanism, the first mechanism and the second mechanism are connected to the end control assembly, and the end control assembly controls the first mechanism and the second mechanism to move through the connection between the first mechanism and end control assembly and the connection between the second mechanism and the end control assembly.

20 Claims, 15 Drawing Sheets

(58) Field of Classification Search

CPC .................. B25J 13/065; B25J 9/0048; G05G 2009/04707; G05G 2009/04766; G05G 9/047

See application file for complete search history.

(56) References Cited

U.S. PATENT DOCUMENTS

| | | | |
|---|---|---|---|
| 6,429,849 B1 | 8/2002 | An et al. | |
| 2002/0040217 A1 | 4/2002 | Jinno | |
| 2004/0024311 A1 | 2/2004 | Quaid, III | |
| 2009/0024142 A1 | 1/2009 | Ruiz Morales | |
| 2009/0248035 A1 | 10/2009 | Sjostedt | |
| 2012/0053701 A1 | 3/2012 | Yi et al. | |
| 2014/0039527 A1 | 2/2014 | Avelar et al. | |
| 2016/0059409 A1 | 3/2016 | Nawrat et al. | |
| 2017/0151028 A1 | 6/2017 | Ogawa et al. | |
| 2018/0353246 A1 | 12/2018 | Ishihara et al. | |
| 2019/0192247 A1* | 6/2019 | Woo ....................... | A61B 34/37 |
| 2020/0015917 A1 | 1/2020 | Cavalier et al. | |
| 2020/0294423 A1 | 9/2020 | Blain et al. | |
| 2020/0356174 A1 | 11/2020 | Andreff et al. | |

FOREIGN PATENT DOCUMENTS

| | | | |
|---|---|---|---|
| CN | 102208150 A | 10/2011 | |
| CN | 102758734 A | 10/2012 | |
| CN | 103386687 A | 11/2013 | |
| CN | 103565529 A | 2/2014 | |
| CN | 103632594 A | 3/2014 | |
| CN | 203619682 U | 6/2014 | |
| CN | 104622585 A | 5/2015 | |
| CN | 104669299 A | 6/2015 | |
| CN | 104690708 A | 6/2015 | |
| CN | 105108762 A | 12/2015 | |
| CN | 105196284 A | 12/2015 | |
| CN | 105662589 A | 6/2016 | |
| CN | 106667583 A | 5/2017 | |
| CN | 107297677 A | 10/2017 | |
| CN | 107321969 A | 11/2017 | |
| CN | 107361848 A | 11/2017 | |
| CN | 107496031 A | 12/2017 | |
| CN | 107595395 A | 1/2018 | |
| CN | 206953010 U | 2/2018 | |
| CN | 207352855 U | 5/2018 | |
| CN | 108742797 A | 11/2018 | |
| CN | 108852514 A | 11/2018 | |
| CN | 109171986 A | 1/2019 | |
| CN | 109621330 A | 4/2019 | |
| CN | 208993750 U | 6/2019 | |
| CN | 110623710 A | 12/2019 | |
| CN | 209790401 U | 12/2019 | |
| CN | 210019449 U | 2/2020 | |
| CN | 111110353 A | 5/2020 | |
| CN | 111329581 A | 6/2020 | |
| CN | 111407409 A | 7/2020 | |
| CN | 111449758 A | 7/2020 | |
| CN | 111604874 A | 9/2020 | |
| CN | 111839740 A | 10/2020 | |
| CN | 111973276 A | 11/2020 | |
| CN | 112349191 A | 2/2021 | |
| CN | 112497234 A | 3/2021 | |
| CN | 113116519 A | 7/2021 | |
| CN | 113208738 A | 8/2021 | |
| CN | 215265162 U | 12/2021 | |
| EP | 3685780 A1 | 7/2020 | |
| GB | 1263424 A | 2/1972 | |
| KR | 20100085621 A | 7/2010 | |
| KR | 20180044524 A | 5/2018 | |
| WO | 2018112227 A2 | 6/2018 | |
| WO | 2019058336 A1 | 3/2019 | |
| WO | 2020188391 A1 | 9/2020 | |
| WO | 2020218678 A1 | 10/2020 | |

OTHER PUBLICATIONS

Written Opinion in PCT/CN2022/075244 mailed on Apr. 14, 2022, 10 pages.

International Search Report in PCT/CN2022/075243 mailed on May 7, 2022, 8 pages.

Written Opinion in PCT/CN2022/075243 mailed on May 7, 2022, 10 pages.

International Search Report in PCT/CN2022/075245 mailed on May 5, 2022, 10 pages.

Written Opinion in PCT/CN2022/075245 mailed on May 5, 2022, 12 pages.

The Extended European Search Report in European Application No. 22745370.1 mailed on May 8, 2024, 7 pages.

The Extended European Search Report in European Application No. 22745368.5 mailed on May 8, 2024, 8 pages.

Partial Supplementary European Search Report in European Application No. 22745369.3 mailed on May 22, 2024, 12 pages.

First Office Action in Chinese Application No. 202110135533.0 mailed on Feb. 28, 2025, 19 pages.

The Second Office Action in Chinese Application No. 202110135533.0 mailed on Aug. 6, 2025, 22 pages.

The Second Office Action in Chinese Application No. 202211025629.2 mailed on Mar. 11, 2026, 19 pages.

\* cited by examiner

<u>200</u>

210

220

230

A

B

200

500

512

522

610

512

500

500

500

720

710

230

ROBOT AND MASTER MANIPULATOR THEREOF

CROSS-REFERENCE TO RELATED APPLICATIONS

This application is a continuation of International Application No. PCT/CN2022/075244, filed on Jan. 30, 2022, which claims priority to Chinese Patent Application No. 202110135533.0, filed on Feb. 1, 2021, and Chinese Patent Application No. 202110454129.X, filed on Apr. 26, 2021, the contents of each of which are incorporated herein by reference.

TECHNICAL FIELD

The present disclosure relates to the field of medical apparatus, and in particular, to a robot and a master manipulator thereof.

BACKGROUND

In recent years, X-ray computed tomography (CT) has made great progress both in basic technology and in new clinical applications. Now CT is no longer a simple imaging examination. CT can be used to cooperate with various clinical departments to achieve various examinations and treatments, and achieve remarkable medical effects. The surgical operation guided by CT image is performed based on CT imaging, which can make real-time judgment and timely adjustment, thereby greatly improving the success rate of surgery, reducing the risk of surgery, and improving the recovery speed and quality of life of patients. However, CT equipment uses X-rays and y-rays to complete imaging work. Performing a surgery on the CT side will expose a doctor to radiation for a long time, posing a great threat to the health of the doctor. Therefore, the master-slave teleoperated robot emerges. The master-slave teleoperated robot is an auxiliary surgical mode as a relatively front-end surgical method. The image-guided robot is controlled by remote operation to perform surgical operations, effectively preventing doctors from being exposed to radiation. However, the current master-slave teleoperated robot cannot simulate the operation of a doctor to control the attitude of surgical tools, which increases the risk and uncertainty of the operation, increases the operation time, reduces the efficiency of the operation, and affects the success rate of the operation. Therefore, it is desirable to provide a master-slave teleoperated robot capable of simulating the operation of a doctor to control the attitude of surgical tools.

SUMMARY

One of the embodiments of the present disclosure provides a master manipulator of a robot. The master manipulator may include an end control assembly; and an attitude adjustment assembly. The attitude adjustment assembly may include a first mechanism and a second mechanism. The first mechanism and the second mechanism may be connected to the end control assembly, and the end control assembly may control the first mechanism and the second mechanism to move through the connection between the first mechanism and end control assembly and the connection between the second mechanism and the end control assembly.

In some embodiments, the first mechanism may include a first rotating transmission bar; the second mechanism may include a second rotating transmission bar; and an angle between a rotation axis of the first rotating transmission bar and a rotation axis of the second rotating transmission bar may be greater than 10°.

In some embodiments, the angle between the rotation axis of the first rotating transmission bar and the rotation axis of the second rotating transmission bar may be greater than 85°.

In some embodiments, the rotation axis of the first rotating transmission bar may intersect with the rotation axis of the second rotating transmission bar.

In some embodiments, the end control assembly may directly apply a force on the first rotating transmission bar and/or the second rotating transmission bar.

In some embodiments, the first rotating transmission bar may be provided with a first guide hole, the second rotating transmission bar may be provided with a second guide hole, and the end control assembly may pass through the first guide hole and the second guide hole.

In some embodiments, the end control assembly may be rotatably connected to a base.

In some embodiments, the master manipulator may further include a first information acquisition device configured to detect a rotation angle of the first mechanism and transmit the rotation angle of the first mechanism to a communication device; and a second information acquisition device configured to detect a rotation angle of the second mechanism and transmit the rotation angle of the second mechanism to the communication device.

In some embodiments, the first information acquisition device may include a first encoder; and the second information acquisition device may include a second encoder.

In some embodiments, the master manipulator may further include a first feedback assembly configured to apply a first attitude adjustment resistance to the first mechanism based on first feedback information; and a second feedback assembly configured to apply a second attitude adjustment resistance to the second mechanism based on second feedback information.

In some embodiments, an end of the first rotating transmission bar may be connected to the first feedback assembly, the first feedback assembly may include a first transmission component and a first feedback motor, and the first feedback motor may be connected to the first rotating transmission bar through the first transmission component; and an end of the second rotating transmission bar may be connected to the second feedback assembly, the second feedback assembly may include a second transmission component and a second feedback motor, and the second feedback motor may be connected to the second rotating transmission bar through the second transmission component.

In some embodiments, the first transmission component may include a first synchronous wheel and a second synchronous wheel. The first synchronous wheel may be connected to the first rotating transmission bar, the second synchronous wheel may be fixed on an output shaft of the first feedback motor, and the first synchronous wheel and the second synchronous wheel may be in transmission connection. The second transmission component may include a third synchronous wheel and a fourth synchronous wheel, the third synchronous wheel may be connected to the second rotating transmission bar, the second synchronous wheel may be fixed on an output shaft of the second feedback motor, and the third synchronous wheel and the fourth synchronous wheel may be in transmission connection.

In some embodiments, the first synchronous wheel and the second synchronous wheel may be in transmission connection through a first rope. A first tensioning member and a second tensioning member may be arranged on a side of the first synchronous wheel along a winding direction of the first rope, and two ends of the first rope may be respectively fixed by the first tensioning member and the second tensioning member. The third synchronous wheel and the fourth synchronous wheel may be in transmission connection through a second rope, a third tensioning member and a fourth tensioning member may be arranged on a side of the third synchronous wheel along a winding direction of the second rope, and two ends of the second rope may be respectively fixed by the third tensioning member and the fourth tensioning member.

In some embodiments, the first mechanism may include a first rotating shaft and a first connecting part, one end of the first connecting part may be connected to the first rotating shaft, and another end of the first connecting part may be movably connected to the end control assembly. The second mechanism may include a second rotating shaft and a second connecting part, one end of the second connecting part may be connected to the second rotating shaft, and another end of the second connecting part may be movably connected to the end control assembly. An angle between an axis of the first rotating shaft and an axis of the second rotating shaft may be greater than 10°.

In some embodiments, the first connecting part and the second connecting part may circumferentially surround the end control assembly.

In some embodiments, the first connecting part may include a first connecting straight rod and a first connecting curved rod, one end of the first connecting curved rod may be connected to the first rotating shaft, another end of the first connecting curved rod may be connected to the first connecting straight rod, and the first connecting straight rod may be movably connected to the end control assembly. The second connecting part may include a second connecting straight rod and a second connecting curved rod, one end of the second connecting curved rod may be connected to the second rotating shaft, another end of the second connecting curved rod may be connected to the second connecting straight rod, and the second connecting straight rod may be movably connected to the end control assembly.

In some embodiments, the angle between the axis of the first rotating shaft and the axis of the second rotating shaft may be greater than 85°.

In some embodiments, the axis of the first rotating shaft may intersect with the axis of the second rotating shaft.

In some embodiments, the master manipulator may further include a third information acquisition device configured to detect a rotation angle of the first mechanism and transmit the rotation angle of the first mechanism to a communication device; and a fourth information acquisition device configured to detect a rotation angle of the second mechanism and transmit the rotation angle of the second mechanism to the communication device.

In some embodiments, the third information acquisition device includes a third encoder; and the fourth information acquisition device includes a fourth encoder.

In some embodiments, the master manipulator may further include a third feedback component configured to apply a third attitude adjustment resistance to the first mechanism based on third feedback information; and a fourth feedback component configured to apply a fourth attitude adjustment resistance to the second mechanism based on fourth feedback information.

In some embodiments, the first rotating shaft may be connected to the third feedback component, the third feedback component may include a third feedback motor and a third transmission component, and the third feedback motor may be connected to the first rotating shaft through the third transmission component. The second rotating shaft may be connected to the fourth feedback component, the fourth feedback component may include a fourth feedback motor and a fourth transmission component, and the fourth feedback motor may be connected to the second rotating shaft through the fourth transmission component.

In some embodiments, the third transmission component may include a fifth synchronous wheel and a sixth synchronous wheel, a radius of the fifth synchronous wheel may be greater than a radius of the sixth synchronous wheel, the fifth synchronous wheel may be connected to the first rotating shaft, the sixth synchronous wheel may be fixedly arranged on an output shaft of the third feedback motor, and the fifth synchronous wheel and the sixth synchronous wheel may be in transmission connection. The fourth transmission component may include a seventh synchronous wheel and an eighth synchronous wheel, a radius of the seventh synchronous wheel may be greater than a radius of the eighth synchronous wheel, the seventh synchronous wheel may be connected to the second rotating shaft, the eighth synchronous wheel may be fixedly arranged on an output shaft of the fourth feedback motor, and the seventh synchronous wheel and the eighth synchronous wheel may be in transmission connection.

In some embodiments, the fifth synchronous wheel and the sixth synchronous wheel may be in transmission connection through a third rope, and a fifth tensioning member may be arranged on a side of the fifth synchronous wheel along a winding direction of the third rope. The seventh synchronous wheel and the eighth synchronous wheel may be in transmission connection through a fourth rope, and a sixth tensioning member may be arranged on a side of the seventh synchronous wheel along a winding direction of the fourth rope.

In some embodiments, the fifth synchronous wheel and the sixth synchronous wheel may be in double-rope transmission connection; and the seventh synchronous wheel and the eighth synchronous wheel may be in double-rope transmission connection.

In some embodiments, a first guide member may be arranged on an upper side of the fifth synchronous wheel along the winding direction of the third rope, so that the third rope on the fifth synchronous wheel may be wound around the sixth synchronous wheel with a first preset pitch. A second guide member may be arranged on an upper side of the seventh synchronous wheel along the winding direction of the fourth rope, so that the fourth rope on the seventh synchronous wheel may be wound around the eighth synchronous wheel with a second preset pitch.

In some embodiments, the attitude adjustment component may further include a locking mechanism.

In some embodiments, the locking mechanism may include a first brake member, configured to lock or unlock a rotation of the first mechanism; and a second brake member, configured to lock or unlock a rotation of the second mechanism.

In some embodiments, the locking mechanism may include a plurality of electromagnets and a plurality of state detection units corresponding to the plurality of electromagnets, the plurality of electromagnets may be arranged along a peripheral side of the end control assembly, and the plurality of state detection units may be configured to detect a plurality of states of the plurality of electromagnets and transmit the plurality of states of the plurality of electromagnets to a communication device. The plurality of electromagnets may be connected to the end control assembly to lock the end control assembly by energizing the plurality of electromagnets, or the plurality of electromagnets may be disconnected from the end control assembly to unlock the end control assembly by de-energizing the plurality of electromagnets.

In some embodiments, the attitude adjustment assembly may further include a plurality of attitude adjustment trigger switches arranged along the peripheral side of the end control assembly.

In some embodiments, the attitude adjustment assembly may further include a plurality of inclination detectors arranged along the peripheral side of the end control assembly, and the plurality of inclination detectors may be configured to detect an inclination of the end control assembly and transmit the inclination of the end control assembly to the communication device.

In some embodiments, the master manipulator may further include a base. The base may include a base body and a rotating platform rotatably connected to the first mechanism and the second mechanism of the attitude adjustment assembly, the rotating platform may be rotatably connected to the base body, the rotating platform may be parallel, relative to a rotating plane of the base body, to a plane where the base body is located, and the rotating platform may be related to a motion of at least one joint of the robot.

In some embodiments, the base may further include a driving member and a transmission assembly, and the driving member may drive, through the transmission assembly, the rotating platform to rotate.

In some embodiments, the transmission assembly may include a worm and a worm gear that mesh with each other, the worm may be connected to an output end of the driving member, and the worm may be fixedly connected to the rotating platform.

In some embodiments, the transmission assembly may include a driving wheel and a driven wheel, a synchronous belt sleeves the driving wheel and the driven wheel, the driving wheel may be connected to an output end of the driving member, and the driven wheel may be fixedly connected to the rotating platform.

In some embodiments, the rotating platform may be provided with a fifth encoder, and the fifth encoder may be configured to detect a rotation angle of the rotating platform and transmit the rotation angle of the rotating platform to a communication device.

In some embodiments, the end control assembly may include an end control force feedback component, and the end control force feedback component may apply a resistance to the end control assembly based on end control force feedback information.

In some embodiments, the end control assembly may include at least one of a puncture needle assembly, a surgical cutting assembly, or a suture assembly.

One of the embodiments of the present disclosure provides a robot. The robot may include a robot body, an end executor, and the master manipulator described in above embodiments. The end executor may be connected to the robot body, the robot body may be electrically connected to a communication device, and the master manipulator may be electrically connected to the communication device and the end executor.

BRIEF DESCRIPTION OF THE DRAWINGS

The present disclosure is further illustrated in terms of exemplary embodiments, and these exemplary embodiments are described in detail with reference to the drawings. These embodiments are not restrictive. In these embodiments, the same number indicates the same structure, wherein.

DETAILED DESCRIPTION

Figure 1:
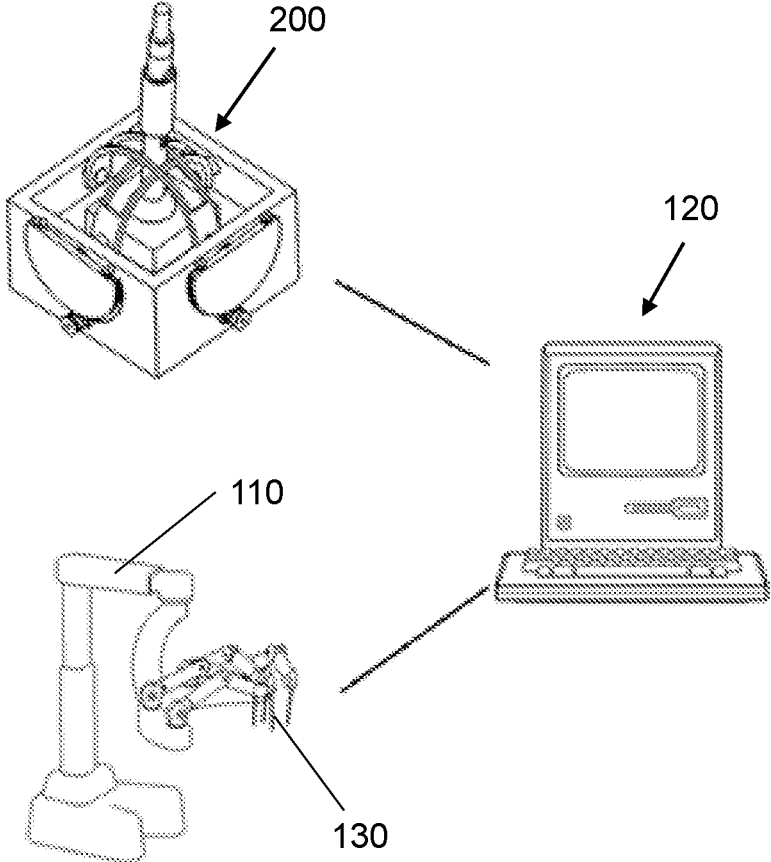
FIG. 1 is a schematic diagram illustrating an exemplary application scenario of a robot according to some embodiments of the present disclosure.

In order to illustrate the technical solutions related to the embodiments of the present disclosure, a brief introduction of the drawings referred to in the description of the embodiments is provided below. Obviously, drawings described below are only some examples or embodiments of the present disclosure. Those having ordinary skills in the art, without further creative efforts, may apply the present disclosure to other similar scenarios according to these drawings. Unless stated otherwise or obvious from the context, the same reference numeral in the drawings refers to the same structure and operation.

It will be understood that the terms "system," "device," "unit," and/or "module" used herein are one method to distinguish different components, elements, parts, sections, or assemblies of different levels in ascending order. However, the terms may be displaced by other expressions if they may achieve the same purpose.

As shown in the present disclosure and claims, unless the context clearly indicates exceptions, the words "a," "an," "one," and/or "the" do not specifically refer to the singular, but may also include the plural. The terms "including" and "comprising" only suggest that the steps and elements that have been clearly identified are included, and these steps and elements do not constitute an exclusive list, and the method or device may also include other steps or elements.

With the continuous advancement of technical research and product development based on medical robots, surgical robots have become one of the important fields in the domain of medical robots. Surgical robot is a medical instrument integrating clinical medicine, biomechanics, mechanics, computer science, microelectronics, and many other disciplines. The surgical robot assists a doctor to perform complex surgical operations in the form of minimally invasive surgery through clear imaging systems and flexible robotic arms, completing intraoperative positioning, cutting, puncture, hemostasis, suturing, and other operations. Under the guidance of a computed tomography (CT) imaging device, an operator uses the surgical robot to assist surgical treatment. However, performing a surgery on the CT side will expose the operator to the radiation for a long time, posing a great threat to health. Therefore, the master-slave telerobot is used to perform surgical operations through teleoperation by controlling and guiding the robot. The current robots often cannot accurately simulate the operation process of the operator, or cannot feedback the magnitude of force. The lack of force perception by the operator increases the risk and uncertainty of surgery, and affects the efficiency of surgery.

In order to solve the above problems, some embodiments of the present disclosure provide a robot for surgery. The robot may include a master manipulator of manipulating an end executor of the robot. The master manipulator may simulate the operation of the operator and provide force feedback, thereby avoiding risks in the surgical process and improving the efficiency of surgery.

FIG. 1 is a schematic diagram illustrating an exemplary application scenario of a robot according to some embodiments of the present disclosure. As shown in FIG. 1, the robot may include a robot body 110, an end executor 130, and a master manipulator 200. The end executor 130 may be connected to the robot body 110 (e.g., arranged at an end of a robotic arm of the robot body 110). The robot body 110 may be electrically connected to a communication device 120. The master manipulator 200 may be electrically connected to the communication device 120 and the end executor 130 to control the end executor 130 to perform a synchronous operation.

When the robot is used in practice, the robot body 110 may be located in a scanning room. Optionally, the robot body 110 may include the robotic arm capable of driving the end executor 130 arranged at an end of the robotic arm to move to adjust an attitude of a functional part at the end of the robotic arm. The end executor 130 may be disposed on the robot body 110 for performing the synchronous operation (e.g., puncturing, suturing, etc.). A control room and the scanning room may be located in two adjacent positions or may be located with a distance. An operating table of an imaging device may be arranged in the control room, and there may be a concrete wall between the operating table and the scanning room to shield the radiation. Moreover, the master manipulator 200 may also be arranged in the control room. A doctor may control the robot body 110 in the scanning room by operating the master manipulator 200 in the control room to complete a master-slave teleoperated operation.

Figure 2:
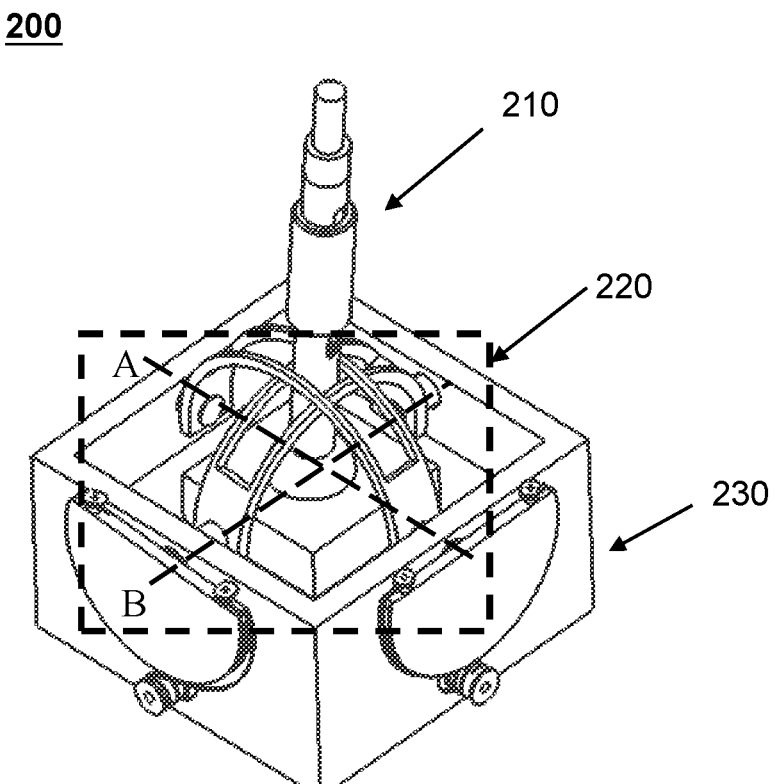
FIG. 2 is a schematic diagram illustrating an exemplary master manipulator according to some embodiments of the present disclosure.

FIG. 2 is a schematic diagram illustrating an exemplary master manipulator 200 according to some embodiments of the present disclosure. Detailed description for the master manipulator 200 in the embodiments of the present disclosure may be described in detail below. It should be noted that the following embodiments are merely used to explain the present disclosure, and do not limit a scope of the present disclosure.

As shown in FIG. 2, the master manipulator 200 of a robot may include an end control assembly 210 and an attitude adjustment assembly 220.

The end control assembly 210 may be configured to control the end executor 130 to perform an operation, such as puncturing and suturing. In some embodiments, the end control assembly 210 may be a hollow columnar structure for easy handling. In some embodiments, the end control assembly 210 may be adaptively designed according to the operating habits of the operator and a structure of the end executor 130 for easy use. For example, the end control assembly 210 may include at least one of a puncture needle assembly, a surgical cutting assembly, or a suture assembly according to different end executors 130 (e.g., a puncture needle, a surgical scissor, a suture needle, etc.), and a shape of the end control assembly 210 may be provided as a shape of a corresponding functional part or another shape facilitating the operation, which may not be limited here.

In some embodiments, the end control assembly 210 may include an end control force feedback component configured to apply a resistance to the end control assembly 210 based on end control force feedback information. The end control force feedback information may include a magnitude of the resistance and a direction of the resistance, or the like. In a specific embodiment, the end executor 130 may be the puncture needle. When the puncture needle is inserted into a patient's body, a human tissue of the patient may generate a reaction force against the puncture needle, i.e., a resistance to puncturing. The resistance may be detected by a sensor arranged on the end executor 130.

In some embodiments, when the end control assembly 210 controls the end executor 130 (e.g., the puncture needle) to perform an operation, and the puncture needle encounters the puncture resistance, the puncture resistance may be fed back to the robot body 110. The robot body 110 may control the end control force feedback component to apply a resistance equivalent to the puncture resistance to the end control assembly 210. In this way, when an operator performs the puncture operation, he/she can feel needle insertion resistance of the puncture needle through the puncture resistance fed back by the end control force feedback component, to truly simulate the situation of holding the needle for puncturing.

In some embodiments, the end control force feedback component may include an actuator motor and a position detection unit. The position detection unit may detect a current position state of a slide block, identify movement displacement of the slide block, and feedback the movement displacement of the slide block to the robot body 110. For example, during the puncture process with the puncture needle, the robot body 110 may control the actuator motor to apply a certain current to generate a torque. A resistance generated by the torque may be consistent with the actual insertion resistance of the puncture needle and acts on the hand of the operator through a slip ring on the end puncture component 210. When the operator moves the slip ring, the resistance may be felt by the operator, thereby realizing a function of feedbacking the puncture force.

When the slip ring of the end control assembly 210 performs a linear motion, the end control force feedback component may detect a distance of the linear motion of the slip ring, and feedback the distance of the linear motion of the slip ring to the robot body 110. The robot body 110 may convert the distance of the linear motion of the slip ring into a linear displacement, through which the robotic arm is controlled to drive the puncture needle to perform the puncture operation. For example, the end control force feedback component may be connected to a roller of a linear motion component. When the roller rotates, the end control force feedback component may detect the distance of the linear motion of the slip ring and feedback the distance of the linear motion of the slip ring to the robot body 110 to control the puncture needle to perform puncturing.

In some embodiments, the master manipulator 200 may be electrically connected to the communication device 120 and the end executor 130, and the communication device 120 may be electrically connected to the robot body 110. Merely by way of example, the resistance information received by the end executor 130 may be transmitted to the robot body 110; and the robot body 110 may send corresponding force feedback information to the master manipulator 200 through the communication device 120 according to the resistance information, thereby realizing a signal transmission. In some embodiments, the communication device 120 may be connected to the master manipulator 200 and the robot body 110 by means of a wired connection, a wireless connection, or a combination thereof. The wired connection may include: a connection via an electrical cable, a fiber optic cable, or a telephone lines, or the like, or any combination thereof. The wireless connection may include: a connection via Bluetooth, Wi-Fi, WiMax, WLAN, ZigBee, a mobile network (e.g., 3G, 4G, or 5G, etc.), or any combination thereof.

The attitude adjustment assembly 220 may be a device for adjusting an attitude of the end control assembly 210. In some embodiments, the attitude adjustment assembly 220 may include a first mechanism and a second mechanism. The first mechanism and the second mechanism may be connected to the end control assembly 210. The end control assembly 210 may control the first mechanism and the second mechanism to move through the connection between the first mechanism and end control assembly and the connection between the second mechanism and the end control assembly. As the first mechanism and the second mechanism are connected to the end control assembly 210, the movement of the first mechanism driven by the end control assembly 210 may have no effect on the second mechanism, and the movement of the second mechanism driven by the end control assembly 210 may have no effect on the first mechanism. The first mechanism and the second mechanism may move independently (e.g., rotate around their rotation axes, respectively, etc.). In some embodiments, the first mechanism and the second mechanism may be the same or similar structures. In some embodiments, the first mechanism and the second mechanism may be configured to convert at least a portion of the movement (e.g., oscillation) of the end control assembly 210 into corresponding movements (e.g., rotation around the rotation axes) of the first mechanism and the second mechanisms. Specifically, the first mechanism may rotate around its rotation axis A with a first degree of rotational freedom, and the second mechanism may rotate around its rotation axis of B with a second degree of rotational freedom. The swing of the end control assembly 210 may drive the first mechanism to rotate around its rotation axis A, and the swing of the end control assembly 210 may drive the second mechanism to rotate around its rotation axis B. An actual attitude adjustment movement of the end control assembly 210 may be a vector sum of rotations of the first mechanism and the second mechanism.

Figure 3:
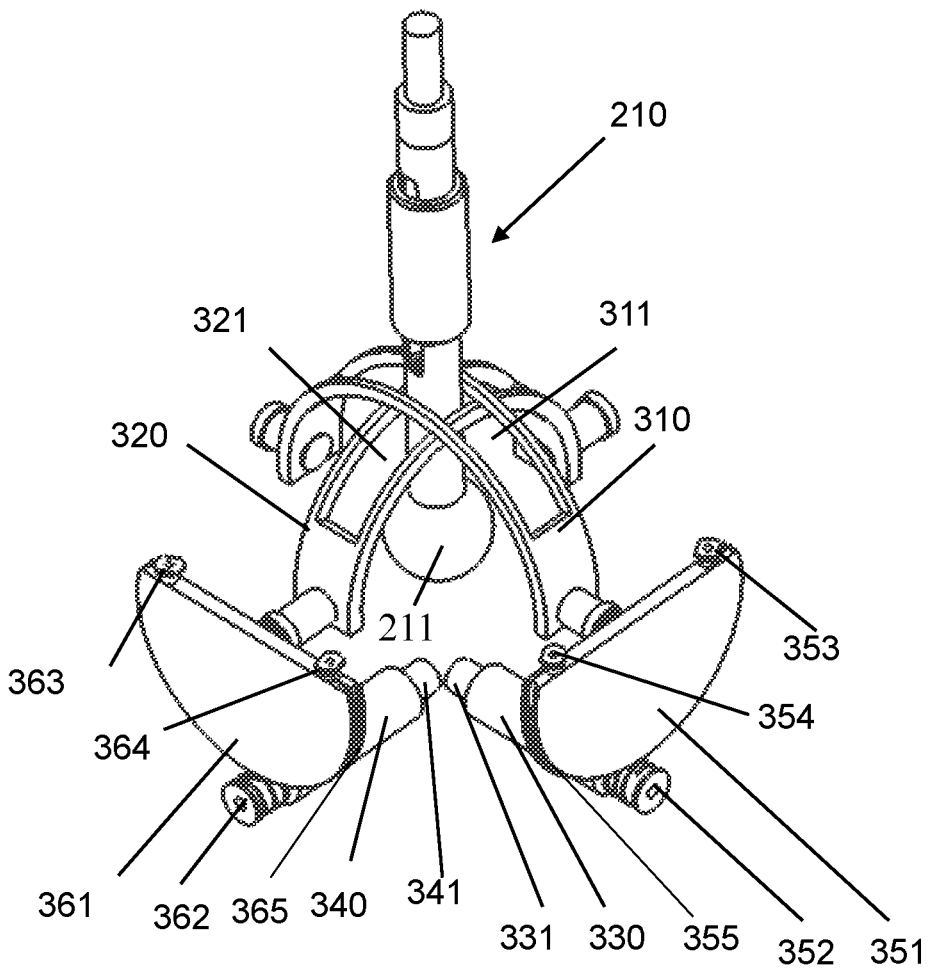
FIG. 3 is a schematic diagram illustrating an exemplary attitude adjustment assembly and an exemplary end control assembly according to some embodiments of the present disclosure.

FIG. 3 is a schematic diagram illustrating an exemplary attitude adjustment assembly 220 and an exemplary end control assembly 210 according to some embodiments of the present disclosure. As shown in FIG. 3, a first mechanism may include a first rotating transmission bar 310; and a second mechanism may include a second rotating transmission bar 320. In some embodiments, the first rotating transmission bar 310 and the second rotating transmission bar 320 may be rotatably arranged on a base 230. For example, the first rotating transmission bar 310 and the second rotating transmission bar 320 may be arranged on the base 230 through a revolving pair, and may rotate around an axis of the revolving pair. In some embodiments, shapes of the first rotating transmission bar 310 and the second rotating transmission bar 320 may be semicircles, to leave a space for installing the end control assembly 210. In some embodiments, the shapes of the first rotating transmission bar 310 and the second rotating transmission bar 320 may also be other shapes, such as straight bars, shapes of a folded line, or irregular shapes, which may not be limited here.

In some embodiments, an angle between a rotation axis of the first rotating transmission bar 310 and a rotation axis of the second rotating transmission bar 320 may be greater than 10°. For example, the angle may be within a range of 10°-180° (e.g., 30°, 60°, or 135°). In some embodiments, the angle between the rotation axis of the first rotating transmission bar 310 and the rotation axis of the second rotating transmission bar 320 may be greater than 85°. For example, the angle between the rotation axis of the first rotating transmission bar 310 and the angle between the rotation axis of the second rotating transmission bar 320 may be 90° as shown in FIG. 3.

In some embodiments, the rotation axis of the first rotating transmission bar 310 may intersect with the rotation axis of the second rotating transmission bar 320. In some embodiments, the rotation axis of the first rotating transmission bar 310 may not intersect with the rotation axis of the second rotating transmission bar 320. When the rotation axis of the first rotating transmission bar 310 intersects with the rotation axis of the second rotating transmission bar 320, a plane where the rotation axis of the first rotating transmission bar 310 and the rotation axis of the second rotating transmission bar 320 are located may or may not be parallel to a horizontal plane.

In some embodiments, the end control assembly 210 may directly apply a force on the first rotating transmission bar 310 and/or the second rotating transmission bar 320, so that the first rotating transmission bar 310 and/or the second rotating transmission bar 320 respectively rotate around their rotation axes. In some embodiments, the first rotating transmission bar 310 may be provided with a first guide hole 311 which may be arranged along a length direction of the first rotating transmission bar 310. In some embodiments, the second rotating transmission bar 320 may be provided with a second guide hole 321 along an extension direction of the second rotating transmission bar 320, and the second guide hole 321 may be arranged along a length direction of the second rotating transmission bar 320. The end control assembly 210 may pass through the first guide hole 311 and the second guide hole 321.

In some embodiments, in order to enable the end control assembly 210 to rotate at a same angle in each direction, the first guide hole 311 may be symmetrical with respect to a middle position of the first rotating transmission bar 310. The second guide hole 321 may be symmetrical with respect to a middle position of the second rotating transmission bar 320. A bottom end of the end control assembly 210 may pass through an intersection position between the first guide hole 311 and the second guide hole 321, and may swing in an extension direction of any one of the first guide hole 311 and the second guide hole 321.

Merely by way of example, when the end control assembly 210 swings in the extension direction of the first guide hole 311, a portion of the end control assembly 210 penetrating through the second rotating transmission bar 320 may push the second rotating transmission bar 320 to rotate with a swing direction of the end control assembly 210. Similarly, when the end control assembly 210 swings in the extension direction of the second guide hole 321, a portion of the end control assembly 210 penetrating through the first rotating transmission bar 310 may push the first rotating transmission bar 310 to rotate with the swing direction of the end control assembly 210. Based on the arrangement mentioned above, when the end control assembly 210 swings in any direction along a movable portion of the base 230, the swing of the end control assembly 210 may be decomposed into motions that the first rotating transmission bar 310 rotates along the rotation axis of the first rotating transmission bar 310, and the second rotating transmission bar 320 rotates along the rotation axis of the second rotating transmission bar 320.

In some embodiments, the end control assembly 210 may be rotatably connected to the base 230. The base 230 refers to a structure for carrying and installing the end control assembly 210 and the attitude adjustment assembly 220. In some embodiments, the end control assembly 210 and the base 230 may be connected through spherical pair. In some embodiments, a bottom of the end control assembly 210 may be provided with a hinge 211. Further, the end control assembly 210 may be pivotally hinged with the base 230 through the hinge 211, so that the end control assembly 210 rotates with respect to the base 230 with the hinge 211 as a center of rotation.

As shown in FIG. 3, a shape of the hinge 211 may be spherical, and a surface connecting the base 230 and the end control assembly 210 may be provided with a spherical groove. The spherical hinge may be rotatably fit in the spherical groove, so that the end control assembly 210 and the base 230 may be connected through a spherical hinge structure. Further, in order to prevent the hinge 211 from detaching from the spherical groove, an opening diameter of the spherical groove may be smaller than a diameter of the hinge 211. In some embodiments, the hinge 211 may also be a universal rotating joint.

In some embodiments, the master manipulator 200 may also include a first information acquisition device and a second information acquisition device. The first information acquisition device may be configured to detect a rotation angle of the first mechanism and transmit the rotation angle of the first mechanism to the communication device 120. The second information acquisition device may be configured to detect a rotation angle of the second mechanism and transmit the rotation angle of the second mechanism to the communication device 120. In some embodiments, the first information acquisition device may include a first encoder 331, and the second information acquisition device may include a second encoder 341.

The encoder refers to a device that encodes and converts a signal or data into a signal for communication, transmission and storage. The encoder usually includes a disk and a reading head. The rotation angle may be detected through the cooperation of the disk and the reading head. In some embodiments, the first encoder 331 and the second encoder 341 may detect rotation angles of output shafts of a first feedback motor 330 and a second feedback motor 340, and feedback the rotation angles to the robot body 110 through the communication device 120. Further, the robot body 110 may control the end executor 130 to adjust a spatial attitude based on the rotation angles, to satisfy the operation requirements.

In some embodiments, the master manipulator 200 may further include a first feedback component and a second feedback component. The first feedback component may be configured to apply a first attitude adjustment resistance to the first mechanism based on first feedback information, and the second feedback component may be configured to apply a second attitude adjustment resistance to the second mechanism based on second feedback information. In some embodiments, the first feedback component may be connected to an end of the first rotating transmission bar 310. The first feedback component may include a first transmission component and a first feedback motor 330. The first feedback motor 330 may be connected to the first rotating transmission bar 310 through the first transmission component. The first encoder 331 may be disposed on the first feedback motor 330. The second feedback component may be connected to an end of the second rotating transmission bar 320. The second feedback component may include a second transmission component and a second feedback motor 340. The second feedback motor 340 may be connected to the second rotating transmission bar 320 through the second transmission component. The second encoder 341 may be disposed on the second feedback motor 340. In some embodiments, the first transmission component may include a first synchronous wheel 351 and a second synchronous wheel 352. The second transmission component may include a third synchronous wheel 361 and a fourth synchronous wheel 362.

Figure 4:
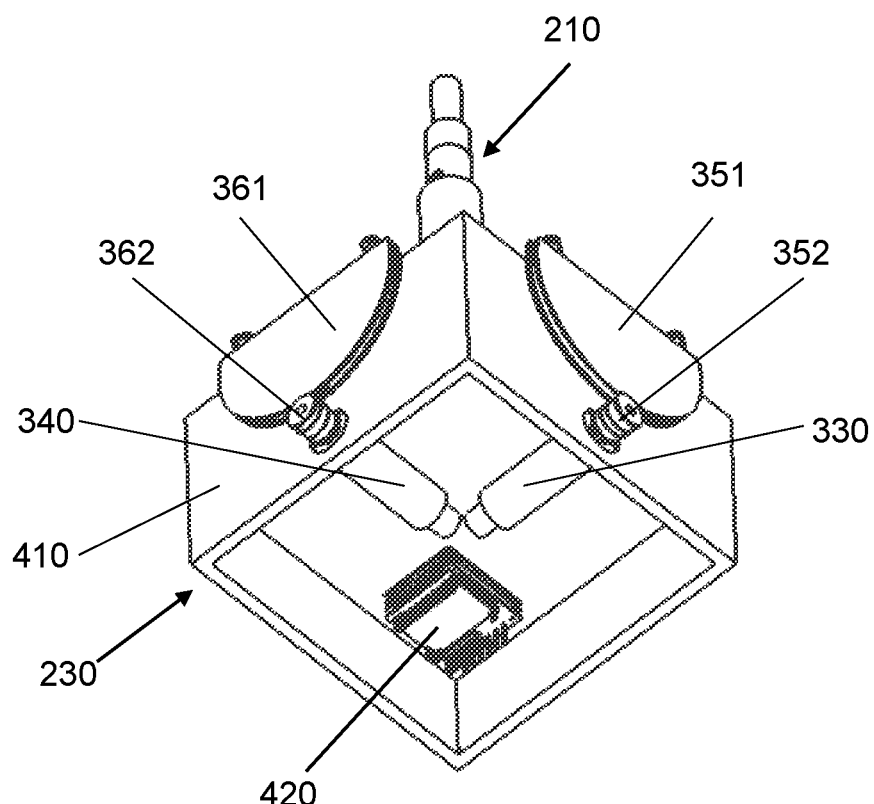
FIG. 4 is a schematic diagram illustrating a bottom view of an exemplary master manipulator according to some embodiments of the present disclosure.

FIG. 4 is a schematic diagram illustrating a bottom view of an exemplary master manipulator 200 according to some embodiments of the present disclosure. As shown in FIG. 4, in order to facilitate the installation of the first feedback motor 330 and the second feedback motor 340, a baffle plate 410 may be provided on an outer side of the base 230. The first synchronous wheel 351 and the third synchronous wheel 361 may be arranged on an outer side of the baffle plate 410 respectively. The first feedback motor 330 and the second feedback motor 340 may be arranged inside the baffle plate 410 and located at a bottom end of the base 230. An output shaft of the first feedback motor 330 and an output shaft of the second feedback motor 340 may protrude out from inside of the baffle plate 410, and may be provided for installing the second synchronous wheel 352 and the fourth synchronous wheel 362, respectively. In some embodiments, an integrated chip 420 may be arranged in an available part of the baffle plate 410. In some embodiments, the integrated chip 420 may include a signal transmission part, etc. The integrated chip 420 may be in communication with the robot body 110 through the communication device 120.

The feedback component refers to a component configured to apply an attitude adjustment resistance. The first feedback component and the second feedback component may respectively apply the first attitude adjustment resistance and the second attitude adjustment resistance to the first rotating transmission bar 310 and the second rotating transmission bar 320 based on first feedback information and second feedback information, respectively. The first feedback information and the second feedback information refer to resistance information in different directions encountered by the end executor 130 when performing an attitude adjustment operation. When an operator adjusts an attitude of the end control assembly 210, the first feedback component may generate an adjustable resistance in a direction opposite to a direction of a rotation trend based on the first feedback information to be fed back to the first rotating transmission bar 310, and the second feedback component may generate an adjustable resistance in a direction opposite to a direction of a rotation trend based on the second feedback information to be fed back to the second rotating transmission bar 320. In different embodiments, the adjustable resistance may be generated in different ways, for example, the adjustable resistance may be generated by electromagnetic rotation between a stator and a rotor, by expansion and contraction of air pressure, by hydraulic extrusion, etc.

Taking the resistance generated by the electromagnetic rotation between the stator and the rotor as an example, an attitude adjustment action for the end control assembly 210 may be decomposed into actions of a rotation of the first rotating transmission bar 310 and a rotation of the second rotating transmission bar 320 through the first mechanism and the second mechanism in a vertical decomposition manner. The rotation of the first rotating transmission bar 310 and the rotation of the second rotating transmission bar 320 may respectively drive the first transmission component and the second transmission component to rotate. The first transmission component and the second transmission component may be respectively connected to the output shafts of the first feedback motor 330 and the second feedback motor 340, so that the rotation of the first transmission component and the rotation of the second transmission component may drive the output shafts of the first feedback motor 330 and the second feedback motor 340 to rotate. When stators of the first feedback motor 330 and the second feedback motor 340 are energized, an electromagnetic action between at least of the stators and at least one of rotors of the first rotating transmission bar 310 and the second rotating transmission bar 320 may apply an electromagnetic force on the at least one stator for rotation, and the electromagnetic force may drives a corresponding output shaft to be in a tendency of rotation, i.e., the resistance is formed. The first feedback motor 330 and the second feedback motor 340 may be configured as that a magnitude of stator current is related to a magnitude of contact force received during an attitude adjustment process. The magnitude of the stator current may be controlled by the robot body 110, thereby adjusting the magnitude of the resistance. The robot body 110 may determine the magnitude of the stator current through the first attitude adjustment resistance or the second attitude adjustment resistance encountered by the end executor 130, so that the first feedback motor 330 or the second feedback motor 340 may apply a resistance equivalent to the first attitude adjustment resistance or the second attitude adjustment resistance at an end of a robotic arm to the first rotating transmission bar 310 or the second rotating transmission bar 320.

In some embodiments, the first transmission component may include the first synchronous wheel 351 and the second synchronous wheel 352. The first synchronous wheel 351 may be connected to the first rotating transmission bar 310, and the second synchronous wheel 352 may be fixedly arranged on the output shaft of the first feedback motor 330. The first synchronous wheel 351 and the second synchronous wheel 352 may be in transmission connection. In some embodiments, the second transmission component may include the third synchronous wheel 361 and the fourth synchronous wheel 362. The third synchronous wheel 361 may be connected to the second rotating transmission bar 320, and the fourth synchronous wheel 362 may be fixedly arranged on the output shaft of the second feedback motor 340. The third synchronous wheel 361 and the fourth synchronous wheel 362 may be in transmission connection. In some embodiments, the first synchronous wheel 351 and the second synchronous wheel 352 may be in transmission connection through a synchronous belt, a steel wire rope, etc. wound around the first synchronous wheel 351 and the second synchronous wheel 352. The third synchronous wheel 361 and the fourth synchronous wheel 362 may be in transmission connection through a synchronous belt, a steel wire rope, etc. wound around the third synchronous wheel 361 and the fourth synchronous wheel 362. The first rotating transmission bar 310 and the second rotating transmission bar 320 may respectively drive the first synchronous wheel 351 and the third synchronous wheel 361 to rotate, thereby driving the second synchronous wheel 352 and the fourth synchronous wheel 362 to rotate.

In some embodiments, the first transmission component and the second transmission component may be in transmission connection through the matching between precision gears, or other ways for transmission, which may not be limited here.

In some embodiments, the first synchronous wheel 351 and the second synchronous wheel 352 may be in transmission connection through a first rope 355 (e.g., a steel wire rope, etc.), a first tensioning member 353 and a second tensioning member 354 may be arranged on a side of the first synchronous wheel 351 along a winding direction of the first rope, and two ends of the first rope may be respectively fixed by the first tensioning member 353 and the second tensioning member 353. In some embodiments, the third synchronous wheel 361 and the fourth synchronous wheel 362 may be in transmission connection through a second rope 365, a third tensioning member 363 and a fourth tensioning member 364 may be arranged on a side of the third synchronous wheel 361 along a winding direction of the second rope, and two ends of the second rope may be respectively fixed by the third tensioning member 363 and the fourth tensioning member 364.

Taking the transmission connection of the first synchronous wheel 351 and the second synchronous wheel 352 as an example, the first synchronous wheel 351 may be a sheet structure enclosed by an arc side with an arc angle greater than 180° and a straight side. A steel wire rope may be arranged on an edge of the arc side. Two ends of the steel wire rope may be respectively fixed on the straight side of the first synchronous wheel 351 through the first tensioning member 353 and the second tensioning member 354. An outer side of the steel wire rope may be coupled with an outer side of the second synchronous wheel 352. In some embodiments, the first tensioning member 353 and the second tensioning member 354 may include fasteners such as bolts and studs, etc. Adjusting the bolts, the studs, etc., may lead to adjustment of a working length of the steel wire rope, so that the steel wire rope works on the synchronous wheel with an appropriate pressure to prevent slipping.

In some embodiments, the transmission connection between the third synchronous wheel 361 and the fourth synchronous wheel 362 may also adopt the same transmission structure as the transmission structure between the first synchronous wheel 351 and the second synchronous wheel 352, which may not be repeated here.

Figure 5:
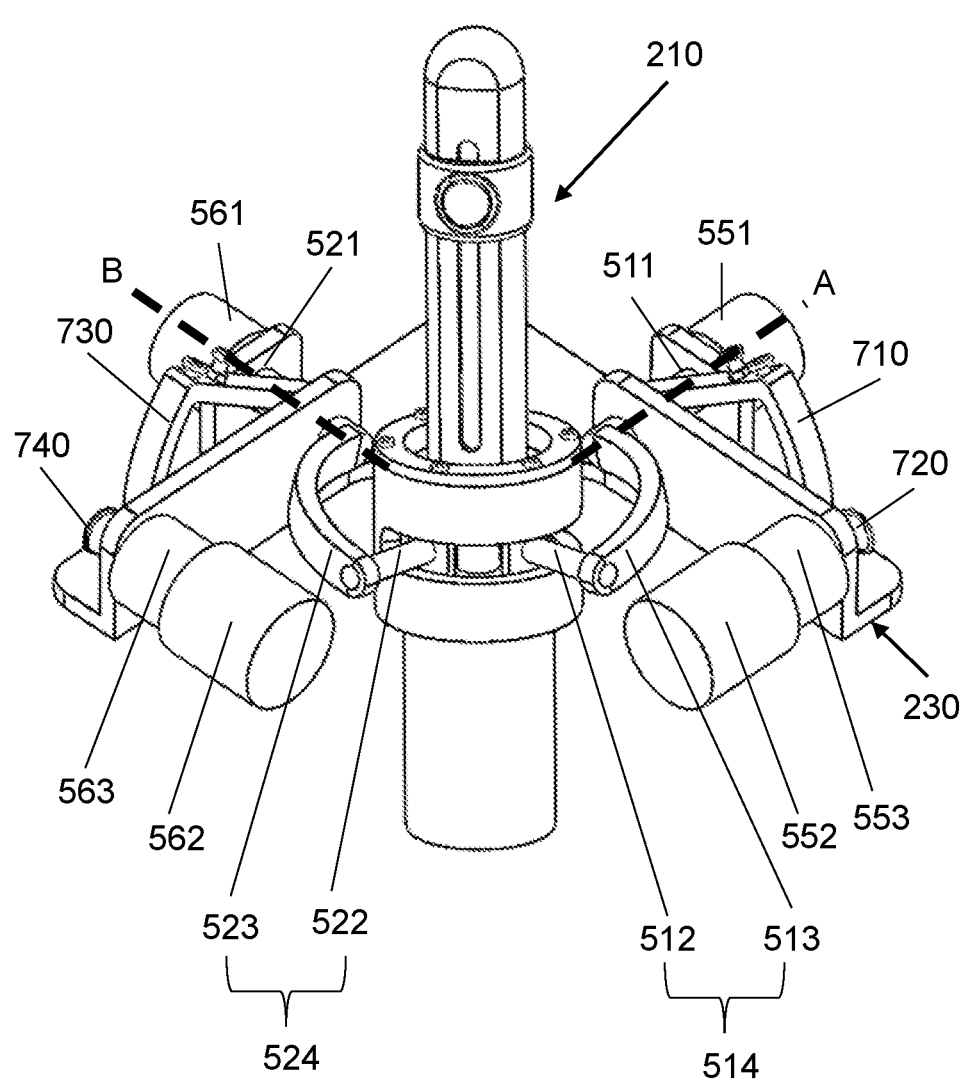
FIG. 5 is another schematic diagram illustrating an exemplary master manipulator according to some embodiments of the present disclosure.

FIG. 5 is another schematic diagram illustrating an exemplary master manipulator 500 according to some embodiments of the present disclosure. The master manipulator 500 in the embodiments of the present disclosure may be described in detail below. It should be noted that the following embodiments are merely used to explain the present disclosure, and do not limit a scope of the present disclosure.

In some embodiments, a first mechanism may include a first rotating shaft 511 and a first connecting part 514. One end of the first connecting part 514 may be connected to the first rotating shaft 511, and another end of the first connecting part 514 may be movably connected to the end control assembly 210. In some embodiments, the first connecting part 514 may include a first connecting straight rod 512 and a first connecting curved rod 513. One end of the first connecting curved rod 513 may connected to the first rotating shaft 511, another end of the first connecting curved rod 513 may be connected to the first connecting straight rod 512, and the first connecting straight rod 512 may be movably connected to the end control assembly 210. In some embodiments, a second mechanism may include a second rotating shaft 521 and a second connecting part 524. One end of the second connecting part 524 may be connected to the second rotating shaft 521, and another end of the second connecting part 524 may be movably connected to the end control assembly 210. In some embodiments, the second connecting part 524 may include a second connecting straight rod 522 and a second connecting curved rod 523. One end of the second connecting curved rod 523 may be connected to the second rotating shaft 521, another end of the second connecting curved rod 523 may be connected to the second connecting straight rod 522, and the second connecting straight rod 522 may be movably connected to the end control assembly 210.

As shown in FIG. 5, the first connecting part 514 and the second connecting part 524 may circumferentially surround the end control assembly 210. Specifically, the first connecting straight rod 512 and the second connecting straight rod 522 may be arranged along a radial direction of the end control assembly 210. The first connecting curved rod 513 and the second connecting curved rod 523 may be circumferentially arranged along an outer side of the end control assembly 210, which makes the structure of the whole device more compact and saves space to a certain extent. In some embodiments, the first connecting curved rod 513 and the second connecting curved rod 523 may also be other shapes, e.g., a straight bar, or the like.

Figure 6:
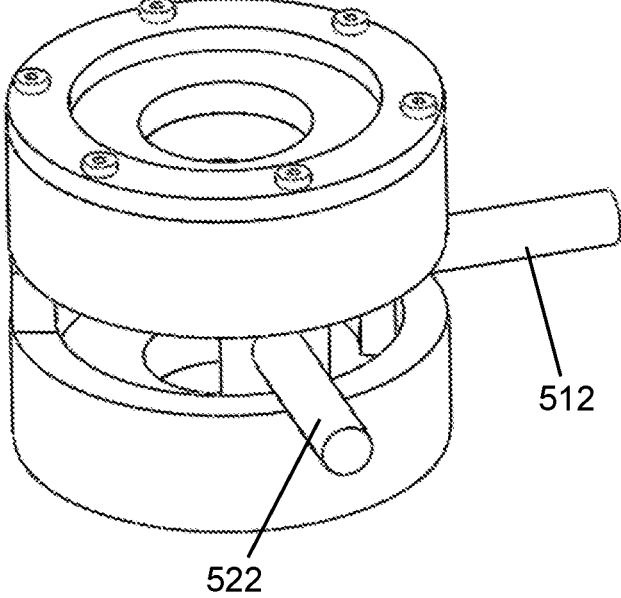
FIG. 6 is a schematic diagram illustrating an exemplary first connecting straight rod and an exemplary second connecting straight rod respectively movably connected to an exemplary end control assembly according to some embodiments of the present disclosure.
Figure 7:
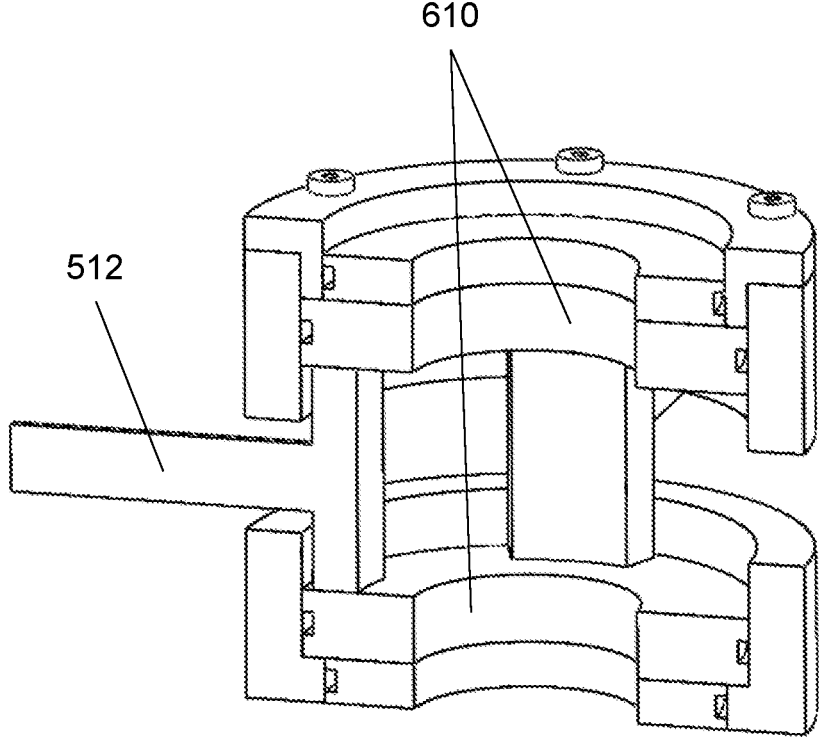
FIG. 7 is a cross-sectional view illustrating an exemplary first connecting straight rod and an exemplary second connecting straight rod respectively movably connected to an exemplary end control assembly according to some embodiments of the present disclosure.

FIG. 6 is a schematic diagram illustrating an exemplary first connecting straight rod 512 and an exemplary second connecting straight rod 522 respectively movably connected to an end control assembly 210 according to some embodiments of the present disclosure. FIG. 7 is a cross-sectional view illustrating an exemplary first connecting straight rod 512 and an exemplary second connecting straight rod 522 respectively movably connected to an exemplary end control assembly 210 according to some embodiments of the present disclosure. For ease of description, a structural relationship of a movable connection between the first connecting part 514 and the end control assembly 210 may be described with the first connecting straight rod 512 used as one end of the first connecting part 514, and a structural relationship of a movable connection between the second connecting part 524 and the end control assembly 210 may be described with the second connecting straight rod 522 used as one end of the second connecting part 524. As shown in FIG. 6, the end control assembly 210 may be provided with chutes for matching the first connecting straight rod 512 and the second connecting straight rod 522. The chutes may be arranged along a circumferential direction of the end control assembly 210. The first connecting straight rod 512 and the second connecting straight rod 522 may be slidably arranged in the chutes. The first connecting straight rod 512 and the second connecting straight rod 522 may rotate around a central axis of the end control assembly 210 along the chutes to realize a flexible connection. The chutes may pass through the entire circumference, or may be merely arranged at a portion region of the circumference with an arc shape. In some embodiments, the first connecting straight rod 512 and the second connecting straight rod 522 may be arranged in a same chute, or may be arranged in different chutes, e.g., the first connecting straight rod 512 and the second connecting straight rod 522 may be arranged in two parallel chutes. In some embodiments, the first connecting straight rod 512 and the second connecting straight rod 522 may be arranged between upper and lower planar thrust bearings 610 as shown in FIG. 7.

Referring to FIG. 5, in some embodiments, the first mechanism may rotate around the rotation axis A of the first rotating shaft 511 and have a first degree of rotational freedom, and the second mechanism may rotate around the rotation axis B of the second rotating shaft 521 and have a second degree of rotational freedom. In some embodiments, an angle between the rotation axis A of the first rotating shaft 511 and the rotation axis B of the second rotating shaft 521 may be greater than 10°. For example, the angle may be determined as an angle within a range of 10-180°. In some embodiments, the angle between the rotation axis A of the first rotating shaft 511 and the rotation axis B of the second rotating shaft 521 may be greater than 85°, e.g., the angle between the rotation axis A of the first rotating shaft 511 and the rotation axis B of the second rotating shaft 521 may be 90°, as shown in FIG. 5. Thus, the first mechanism and the second mechanism may obtain a relatively large operating space.

In some embodiments, the rotation axis A of the first rotating shaft 511 may or may not intersect with the rotation axis B of the second rotating shaft 521. When the rotation axis A of the first rotating shaft 511 intersect with the rotation axis B of the second rotating shaft 521, the plane where the rotation axis A of the first rotating shaft 511 and the rotation axis B of the second rotating shaft 521 is located may or may not be parallel to the horizontal plane.

For ease of description, a motion relationship with the end control assembly 210 may be described with the first connecting straight rod 512 and the first connecting curved rod 513 used as the first connecting parts 514. Similarly, the motion relationship with the end control assembly 210 may be described with the second connecting straight rod 522 and the second connecting curved rod 523 used as the second connecting parts 524. Merely by way of example, when the end control assembly 210 rotates around the rotation axis A of the first rotating shaft 511, the first connecting straight rod 512 may drive the first connecting curved rod 513 to rotate around the rotation axis A of the first rotating shaft 511 with a swing direction of the end control assembly 210. Similarly, when the end control assembly 210 rotates around the rotation axis A of the second rotating shaft 521, the second connecting rod 523 may drive the second connecting curved rod to around the rotation axis B of the second rotating shaft 521 with the swing direction of the end control assembly 210. Based on this structure, when the end control assembly 210 swings in any direction, the swing of the end control assembly may be decomposed into a rotation around the rotation axis A of the first rotating shaft 511 and a rotation around the rotation axis B of the second rotating shaft 521 in a decomposed manner.

Figure 8:
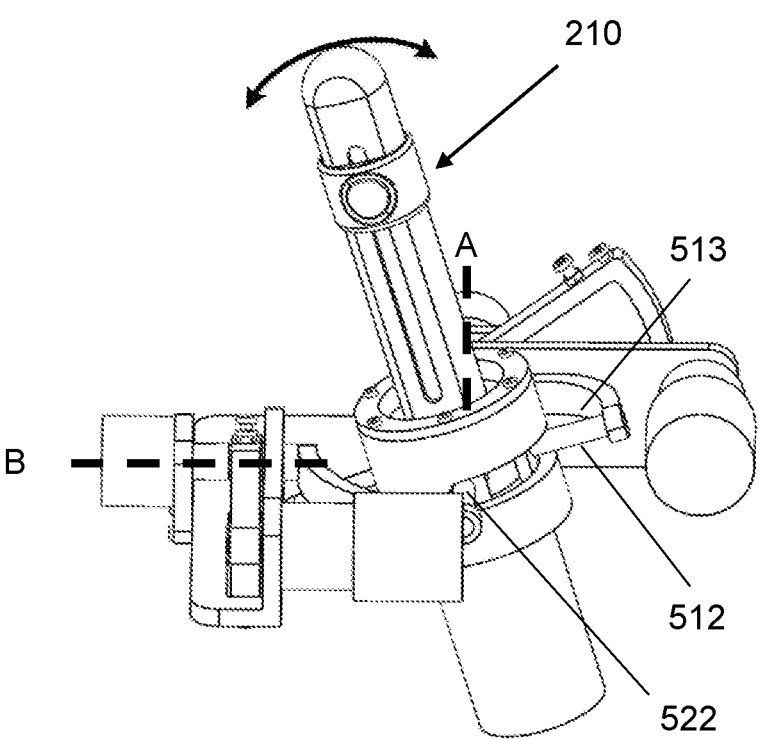
FIG. 8 is a schematic diagram illustrating an exemplary attitude adjustment of a master manipulator according to some embodiments of the present disclosure.

FIG. 8 is a schematic diagram illustrating an exemplary attitude adjustment of a master manipulator 500 according to some embodiments of the present disclosure. As shown in FIG. 8, the end control assembly 210 may merely swing around the rotation axis A of the first rotating shaft 511 (left and right directions in FIG. 8). The first connecting straight rod 512 may drive the first connecting curved rod 513 to rotate around the rotation axis A of the first rotating shaft 511 to realize the attitude adjustment with a single degree of freedom (the first degree of rotational freedom).

Figure 9:
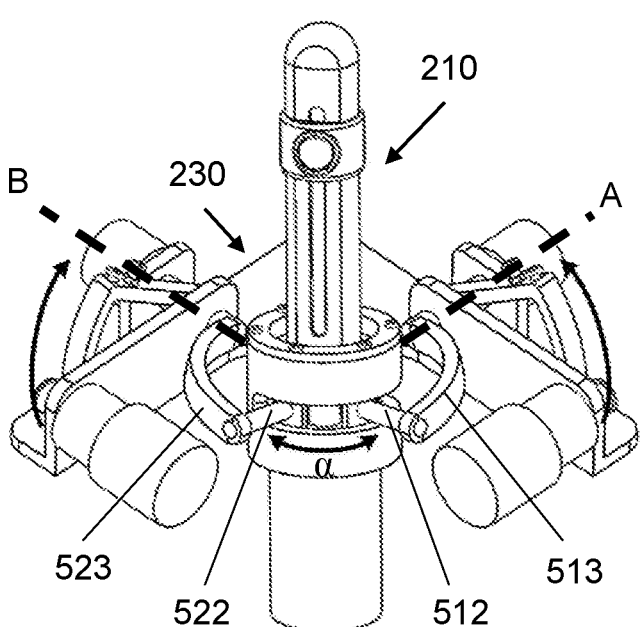
FIG. 9 is another schematic diagram illustrating an exemplary attitude adjustment of a master manipulator according to some embodiments of the present disclosure.

FIG. 9 is another schematic diagram illustrating an exemplary attitude adjustment of a master manipulator 500 according to some embodiments of the present disclosure. As shown in FIG. 9, with the first connecting straight rod 513 and the second connecting curved rod 523 horizontal, and the end control assembly 210 perpendicular to the horizontal plane as a zero position of the master manipulator 500 (a state before attitude adjustment), the end control assembly 210 may inwardly swing to paper in FIG. 9, the first connecting straight rod 512 may drive the first connecting curved rod 513 to rotate counterclockwise around the rotation axis A of the first rotating shaft 511, and the second connecting straight rod 522 may drive the second connecting curved rod 523 to rotate clockwise around the rotation axis B of the second rotating shaft 521. In some embodiments, the first rotating shaft 511 and the second rotating shaft 521 may be arranged on the base 230, and positions of the first rotating shaft 511 and the second rotating shaft 521 relative to the base 230 may not change. When the end control assembly 210 inwardly swing to make the first connecting curved rod 513 and the second connecting curved rod 523 rotate around the rotation axis A and the rotation axis B respectively, a position of a connecting end of the first connecting curved rod 513 and the first connecting straight rod 512 and a position of a connecting end of the second connecting curved rod 523 and the second connecting straight rod 522 and the end control assembly 210 may move relatively, so that an angle α between the first connecting straight rod 512 and the second connecting straight rod 522 may gradually decrease.

Figure 10:
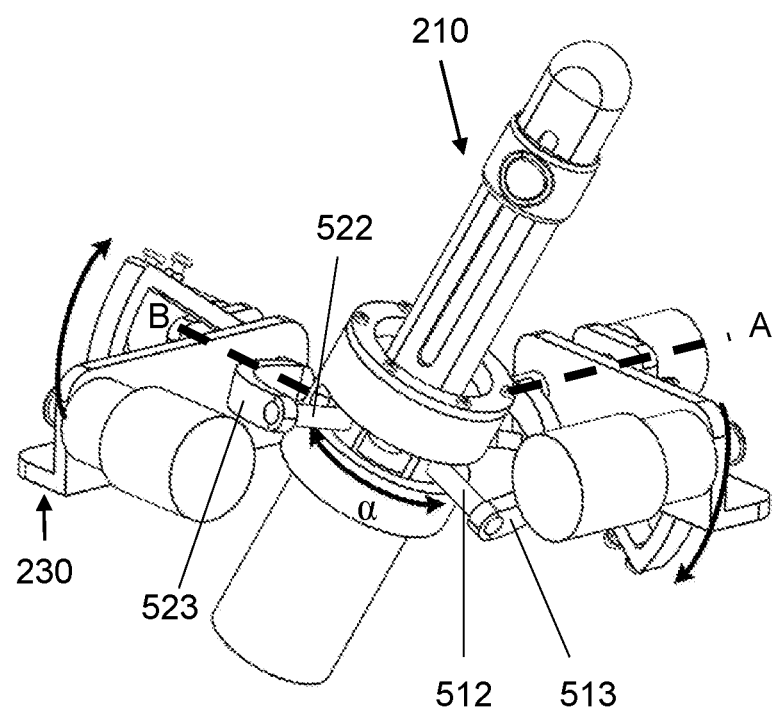
FIG. 10 is another schematic diagram illustrating an exemplary attitude adjustment of a master manipulator according to some embodiments of the present disclosure.

FIG. 10 is another schematic diagram illustrating an exemplary attitude adjustment of a master manipulator 500 according to some embodiments of the present disclosure. As shown in FIG. 10, taking the first connecting curved rod 513 and the second connecting curved rod 523 being horizontal, and the end control assembly 210 perpendicular to the horizontal plane as a zero position of the master manipulator 500 (a state before attitude adjustment), the end control assembly 210 may swing to the right as shown in FIG. 9, the first connecting straight rod 512 may drive the first connecting curved rod 513 to rotate clockwise around the rotation axis A of the first rotating shaft 511, and the second connecting straight rod 522 may drive the second connecting curved rod 523 to rotate clockwise around the rotation axis B of the second rotating shaft 521. In some embodiments, the first rotating shaft 511 and the second rotating shaft 521 may be arranged on the base 230, and positions of the first rotating shaft 511 and the second rotating shaft 521 relative to the base 230 may not change. When the end control assembly 210 swing to the right to make the first connecting curved rod 513 and the second connecting curved rod 523 rotate around the rotation axis A and the rotation axis B respectively, a position of a connecting end between the first connecting curved rod 513 and the first connecting straight rod 512 and a position of a connecting end between the second connecting curved rod 523 and the second connecting straight rod 522 and the end control assembly 210 may move relatively, so that an angle α between the first connecting straight rod 512 and the second connecting straight rod 522 may gradually increase.

Referring to FIG. 5, in some embodiments, the master manipulator 500 may further include a third information acquisition device and a fourth information acquisition device. The third information acquisition device may detect a rotation angle of the first mechanism and transmit the rotation angle of the first mechanism to the communication device. The fourth information acquisition device may detect a rotation angle of the second mechanism and transmit the rotation angle of the second mechanism to the communication device. In some embodiments, the third information acquisition device may include a third encoder 551, and the fourth information acquisition device may include a fourth encoder 561.

The encoder refers to a device that encodes and converts a signal or data into a signal form for communication, transmission and storage. The third encoder 551 and the fourth encoder 561 may include a magnetic disk and a reading head. Rotation angles of the first connecting part 514 and the second connecting part 524 may be detected through the cooperation of the magnetic disk and the reading head. The third encoder 551 and the fourth encoder 561 may respectively feedback the rotation angles of the first connecting part 514 and the second connecting part 524 to the robot body 110 through the communication device 120, and the robot body 110 may control the end executor 130 to adjust a spatial attitude based on the rotation angles of the first connecting part 514 and the second connecting part 524 to satisfy the operation requirements.

In some embodiments, the master manipulator 500 may further include a third feedback component and a fourth feedback component. The third feedback component may be configured to apply a third attitude adjustment resistance to the first mechanism based on third feedback information. The fourth feedback component may be configured to apply a fourth attitude adjustment resistance to the second mechanism based on fourth feedback information. In some embodiments, the third feedback component may be connected to the first rotating shaft 511. The third feedback component may include a third feedback motor 552 and a third transmission component, and the third feedback motor 552 may be connected to the first rotating shaft through the third transmission component 511. The third encoder 551 may be disposed at an end of the first rotating shaft 511. The fourth feedback component may be connected to the second rotating shaft 521. The fourth feedback component may include a fourth feedback motor 562 and a fourth transmission component, and the fourth feedback motor 562 may be connected to the second rotating shaft 521 through the fourth transmission component. The fourth encoder 561 may be disposed at an end of the second rotating shaft 521. In some embodiments, the third transmission component may include a fifth synchronous wheel 710 and a sixth synchronous wheel 720, and the fourth transmission component may include a seventh synchronous wheel 730 and an eighth synchronous wheel 740.

The feedback component refers to a component configured to apply an attitude adjustment resistance. The third feedback component and the fourth feedback component may respectively apply the third attitude adjustment resistance and the fourth attitude adjustment resistance to the first rotating shaft 511 and the second rotating shaft 521 based on the third feedback information and the fourth feedback information. The third feedback information and the fourth feedback information refer to resistance information in different directions encountered by the end executor 130 when performing an attitude adjustment operation. When the end executor 130 encounters the third attitude adjustment resistance or the fourth attitude adjustment resistance, the third attitude adjustment resistance or the fourth attitude adjustment resistance may be fed back to the master manipulator 500 through the communication device 120, the third feedback motor 552 or the fourth feedback motor 562 may receive the third feedback information or the fourth feedback information, and apply a resistance equivalent to the third attitude adjustment resistance or the fourth attitude adjustment resistance of the end executor 130 to the first rotating shaft 511 and the second rotating shaft 521 through the third transmission component or the fourth transmission component, to realize attitude adjustment force feedback of the end executor 130. In this way, when an operator drives the end control assembly 210 to rotate, the operator may feel the resistance opposite to the rotation direction, thereby realizing force feedback during attitude adjustment.

Figure 11:
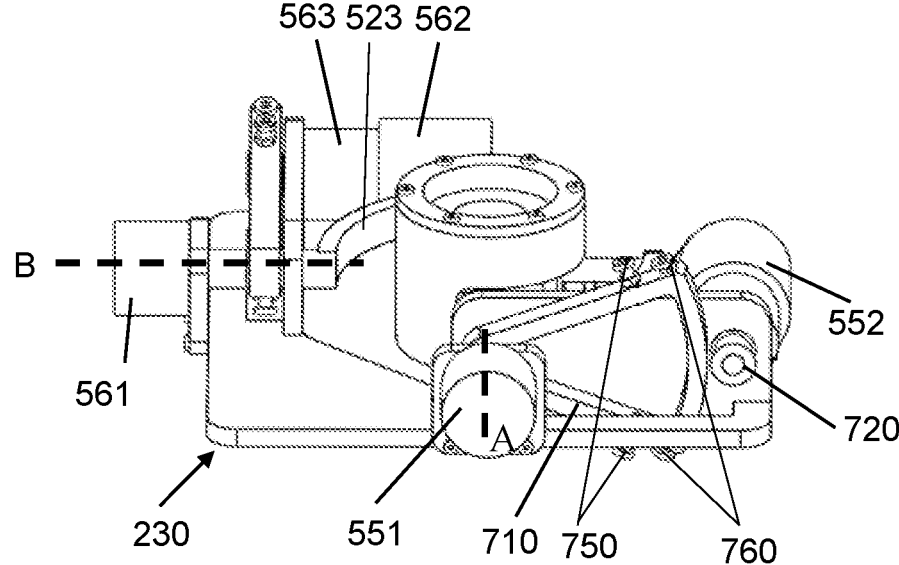
FIG. 11 is a schematic diagram illustrating an exemplary third transmission component and an exemplary fourth transmission component according to some embodiments of the present disclosure.

FIG. 11 is a schematic diagram illustrating an exemplary third transmission component and an exemplary fourth transmission component according to some embodiments of the present disclosure. As shown in FIG. 11, the third transmission component may include the fifth synchronous wheel 710 and the sixth synchronous wheel 720. The fifth synchronous wheel 710 may be connected to the first rotating shaft 511 (not shown in FIG. 11), and the sixth synchronous wheel 720 may be fixedly arranged on an output shaft of the third feedback motor 552. The fifth synchronous wheel 710 and the sixth synchronous wheel 720 may be in transmission connection. The fourth transmission component may include the seventh synchronous wheel 730 and the eighth synchronous wheel 740 (not shown in FIG. 11). The seventh synchronous wheel 730 may be connected to the second rotating shaft 521, and the eighth synchronous wheel 740 may be fixedly arranged on an output shaft of the fourth feedback motor 562. The seventh synchronous wheel 730 and the eighth synchronous wheel 740 may be in transmission connection. In some embodiments, the fifth synchronous wheel 710 and the sixth synchronous wheel 720 may realize the transmission connection through a synchronous belt, a steel wire rope, etc., wound around the fifth synchronous wheel 710 and the sixth synchronous wheel 720. The seventh synchronous wheel 730 and the eighth synchronous wheel 740 may also realize the transmission connection through a synchronous belt, a steel wire rope, etc. wound around the seventh synchronous wheel 730 and the eighth synchronous wheel 740. The first rotating shaft 511 and the second rotating shaft 521 may respectively drive the fifth synchronous wheel 710 and the seventh synchronous wheel 730 to rotate, thereby driving the sixth synchronous wheel 720 and the eighth synchronous wheel 740 to rotate.

In some embodiments, the third transmission component and the fourth transmission component may also use the cooperation between precision gears for transmission, or may use other ways to cooperate with the transmission, which may not be limited here.

In some embodiments, a radius of the fifth synchronous wheel 710 may be greater than a radius of the sixth synchronous wheel 720. A radius of the seventh synchronous wheel 730 may be greater than a radius of the eighth synchronous wheel 740. In some embodiments, a ratio of the radius of the fifth synchronous wheel 710 to the radius of the sixth synchronous wheel 720 may be 10:1. A ratio of the radius of the seventh synchronous wheel 730 to the radius of the eighth synchronous wheel 740 may be 10:1. The ratio of different radiuses refers to a transmission ratio, and the transmission ratio may be determined based on an attitude adjustment load. Compared with a mechanism in series, a transmission ratio between the synchronous wheels of a mechanism in parallel needs to be increased as much as possible, so that a size of a motor of the mechanism in parallel is determined as small as possible with the same attitude adjustment load requirements, and a direct current (DC) brush motor is preferably selected for force feedback.

In some embodiments, the fifth synchronous wheel 710 and the sixth synchronous wheel 720 may be in transmission connection through a third rope (e.g., the steel wire rope, etc.). A fifth tensioning member 750 may be arranged on a side of the fifth synchronous wheel 710 along a winding direction of the third rope for tensioning and fixing the third rope. In some embodiments, the seventh synchronous wheel 730 and the eighth synchronous wheel 740 may be in transmission connection through a fourth rope. A sixth tensioning member (not shown) may be arranged on a side of the seventh synchronous wheel 730 along a winding direction of the fourth rope for tensioning and fixing the fourth rope.

Taking the transmission connection of the fifth synchronous wheel 710 and the sixth synchronous wheel 720 as an example, a structure of the fifth synchronous wheel 710 may be a fan-shaped sheet structure, of which two right-angled sides may be both provided with the fifth tensioning members 750. Two ends of the steel wire rope for connecting the fifth synchronous wheel 710 and the sixth synchronous wheel 720 may be respectively fixed by the two fifth tensioning members 750, and an outer side of the steel wire rope for connecting the fifth synchronous wheel 710 and the sixth synchronous wheel 720 may be coupled with an outer side of the sixth synchronous wheel 720. In some embodiments, the fifth tensioning member 750 and the sixth tensioning member may include fasteners such as tension bolts, lock nuts, or the like. A working length of the third rope may be adjusted by adjusting the tensioning member, so that the third rope works on the synchronous wheel with a suitable pressure to prevent the rope from slipping during work.

Figure 12:
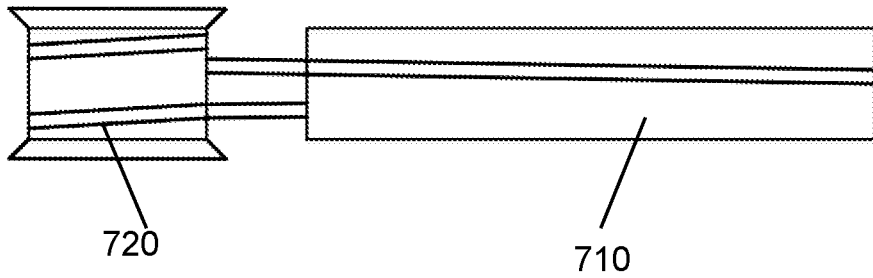
FIG. 12 is a schematic diagram illustrating an exemplary double-rope transmission connection according to some embodiments of the present disclosure.

FIG. 12 is a schematic diagram illustrating an exemplary double-rope transmission connection according to some embodiments of the present disclosure. In some embodiments, the fifth synchronous wheel 710 and the sixth synchronous wheel 720 may be in double-rope transmission connection. The seventh synchronous wheel 730 and the eighth synchronous wheel 740 may also be in double-rope transmission connection, as shown in FIG. 12. Taking the steel wire rope as an example, if a steel wire rope is used for transmission, a transmission stiffness of the steel wire rope needs to be increased by increasing a diameter of the steel wire rope, and a single wire diameter of the steel wire rope (i.e., a diameter of a smallest unit that makes up the steel wire rope) may increase synchronously, and then diameters of the sixth synchronous wheel 720 and the eighth synchronous wheel 740 may also need to be increased synchronously (since there is a linear relationship for meeting a service life between the single wire diameter of the steel wire rope and the diameters of the sixth synchronous wheel 720 and the eighth synchronous wheel 740), which in turn affects the transmission ratio. However, the diameters of the sixth synchronous wheel 720 and the eighth synchronous wheel 740 may not need to be changed if the double-rope transmission connection is adopted to connect the sixth synchronous wheel 720 and the eighth synchronous wheel 740, and thus the transmission stiffness of the steel wire rope in the double-rope transmission connection may be doubled while keeping the transmission ratio constant.

In some embodiments, a first guide member 760 may be provided on an upper edge of the fifth synchronous wheel 710 along the winding direction of the third rope, so that the third rope (e.g., the steel wire rope, etc.) on the fifth synchronous wheel 710 may be wound around the sixth synchronous wheel 720 with a first preset pitch. In some embodiments, a second guide member may be provided on an upper edge of the seventh synchronous wheel 730 along the winding direction of the fourth rope, so that the fourth rope on the seventh synchronous wheel 730 may be wound around the eighth synchronous wheel 740 with a second preset pitch. The first guide member 760 may be a structure such as a guide column.

Figure 13:
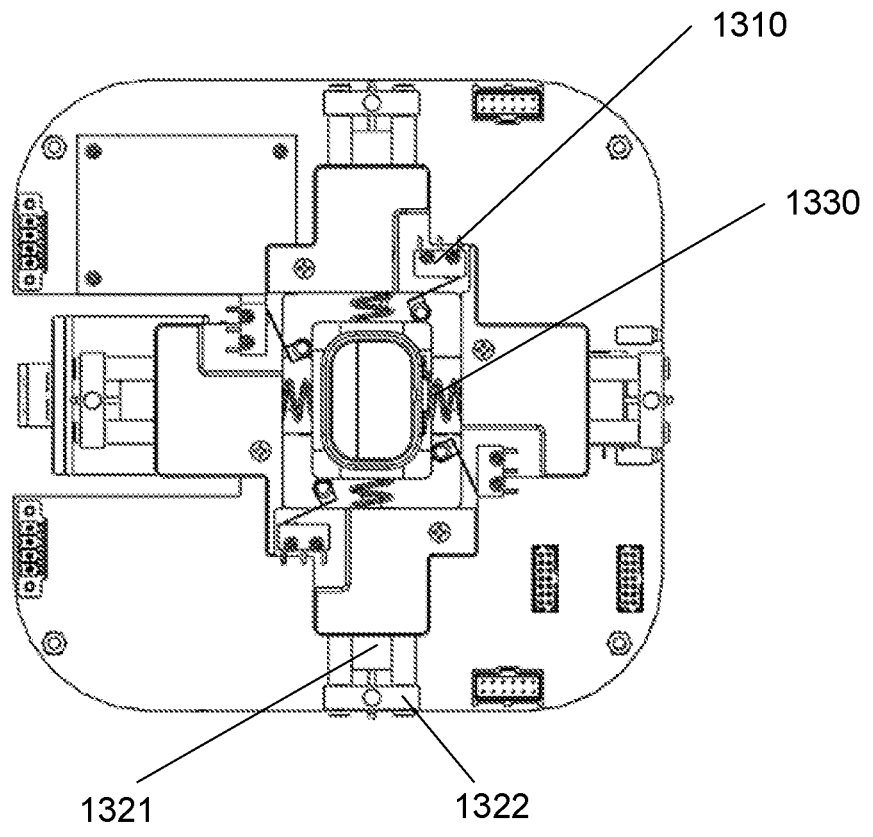
FIG. 13 is a top view illustrating an exemplary master manipulator according to some embodiments of the present disclosure.

FIG. 13 a top view illustrating an exemplary master manipulator according to some embodiments of the present disclosure. As shown in FIG. 13, the attitude adjustment assembly 220 may include a locking mechanism configured to lock or unlock an attitude of the end control assembly 210. The end control assembly 210 may move after the locking mechanism unlocking the end control assembly 210. In some embodiments, the locking mechanism may enable locking and unlocking of the end control assembly 210. The locking mechanism may be fixedly arranged in the attitude adjustment assembly 220, or fixedly arranged on the base 230. In some embodiments, the locking mechanism may implement locking/unlocking by contacting with/separating from the end control assembly 210. When the locking mechanism locks the end control assembly 210, the end control assembly 210 cannot move, and thus a spatial attitude of the end executor 130 (e.g., the puncture needle, etc.) cannot be adjusted. Specifically, the locking mechanism may respectively lock the end control assembly 210 with respect to the first mechanism and the second mechanism. For example, the locking mechanism may prevent the end control assembly 210 from rotating around the rotation axis A of the first mechanism, and in this case, the motion of the second mechanism around the rotation axis B thereof may not be affected. As another example, the locking mechanism may prevent the end control assembly 210 from rotating around the rotation axis B of the second mechanism, and in this case, the motion of the first mechanism around the rotation axis A thereof may not be affected. As another example, the locking mechanism may prevent the end control assembly 210 from rotating around the rotation axis A of the first mechanism and the rotation axis B of the second mechanism. In this case, the end control assembly 210 may form a fixed whole with respect to the first mechanism and the second mechanism. In some embodiments, the whole of the end control assembly 210 formed with respect to the first mechanism and the second mechanism may rotate around a perpendicular line of a plane where the base 230 is located with respect to the base 230, and the rotation may be limited by the locking mechanism. In some embodiments, the end control assembly 210 may rotate around a central axis of the end control assembly 210, and the rotation may be limited by the locking mechanism. When the spatial attitude of the end executor 130 needs to be adjusted, the locking mechanism may perform unlock the end control assembly 210. In this case, the end control assembly 210 may move to adjust the spatial attitude of the end executor 130. When the end executor 130 is aligned with a target point, the locking mechanism may lock the end control assembly 210, so that the spatial attitude of the end executor 130 may not change any more, preventing the end control assembly 210 from continuing to move and affecting the spatial attitude of the end executor 130.

Referring to FIG. 5, in some embodiments, the locking mechanism may include a first brake member 553 and a second brake member 563. The first brake 553 may lock/unlock a rotation of the first mechanism, and the second brake member may 563 lock/unlock a rotation of the second mechanism. The first brake member 553 and the second brake member 563 may be respectively arranged on the output shafts of the third feedback motor 552 and the fourth feedback motor 562 to lock the output shafts of the third feedback motor 552 and/or the fourth feedback motor 562 and prevent the output shafts of the third feedback motor 552 and/or the fourth feedback motor 562 from rotating, thereby limiting the rotation of the first mechanism around its rotation axis and/or limiting the rotation of the second mechanism around its rotation axis. In some embodiments, the first brake member 553 and the second brake member 563 may be clasp brakes.

In some embodiments, the locking mechanism may include a plurality of electromagnets 1321 and a plurality of state detection units 1322 corresponding to the plurality of electromagnets 1321. The plurality of electromagnets 1321 may be arranged along a peripheral side of the end control assembly 210. The plurality of electromagnets may be connected to the end control assembly 210 to lock the end control assembly 210 by energizing the plurality of electromagnets, or the plurality of electromagnets may be disconnected from the end control assembly 210 to unlock the end control assembly 210 by de-energizing the plurality of electromagnets. The plurality of state detection units may be configured to detect states of the plurality of electromagnets 1321 and transmit the states of the plurality of electromagnets 1321 to the communication device 120.

In some embodiments, the plurality of electromagnets 1321 may control an extension shaft that extends to abut against the end control assembly 210, to limit the motion of the end control assembly 210. Extension of the extension shaft may be controlled by energizing the plurality of electromagnets 1321, and retraction of the extension shaft may be controlled by de-energizing the plurality of electromagnets 1321. Specifically, the extension shaft may extend when the plurality of electromagnets 1321 are energized, or the extension shaft may extend when the plurality of electromagnets 1321 are de-energized. The plurality of state detection units 1322 may be configured to detect a working state of the plurality of electromagnets 1321, i.e., to detect whether the plurality of electromagnets 1321 are energized or de-energized, to know whether the extension shaft extends accordingly. Merely by way of example, when the plurality of electromagnets 1321 are energized, the extension shaft may be in contact with the end control assembly 210 to limit the rotation of the end control assembly 210 toward the extension shaft. When the plurality of electromagnets 1321 are de-energized, the extension shaft may retract and no longer touch the end control assembly 210. In this case, the restraint of the end control assembly 210 toward the extension shaft may be released, and the end control assembly 210 may move toward the direction where the extension shaft is located.

In some embodiments, there may be the plurality of electromagnets 1321 which are evenly distributed along the peripheral side of the end control assembly 210. Merely by way of example, there may be four electromagnets 1321 which may be evenly distributed along the peripheral side the end control assembly 210. The end control assembly 210 may be locked when the four electromagnets 1321 extend out. In some embodiments, the plurality of electromagnets 1321 may be fixed by threads, or other components. In some embodiments, an elastic support part 1330 (e.g., a spring, etc.) may be provided on the peripheral side of the end control assembly 210. The elastic support part 1330 may keep the end control assembly 210 in a vertical state when the plurality of electromagnets 1321 retract and provide recovery force for movement during attitude adjustment.

In some embodiments, the plurality of state detection units 1322 may detect the working state of the plurality of electromagnets 1321 in real time and feedback the working state of the plurality of electromagnets 1321 to the robot body 110. The plurality of state detection units 1322 may detect whether the plurality of electromagnets 1321 work normally, thereby improving the safety of the whole device. Merely by way of example, when the plurality of electromagnets 1321 are de-energized, the plurality of state detection units 1322 may detect t that the plurality of electromagnets 1221 make the extension shaft be in an extended state. In this case, the plurality of state detection units 1322 may feedback a signal indicating that the end control assembly 210 is locked to the robot body 110, indicating that the end control assembly 210 cannot move. When the plurality of electromagnets 1321 are energized, the plurality of state detection units 1322 may detect that the plurality of electromagnets 1221 make the extension shaft be in a retracted state. In this case, the plurality of state detection units 1322 may feedback a signal indicating that the end control assembly 210 is unlocked to the robot body 110, indicating that the end control assembly 210 can move. In some embodiments, the plurality of state detection units 1322 may be photoelectric switches, or other components capable of detecting the state of the plurality of electromagnets 1321.

In some embodiments, the attitude adjustment assembly 220 may further include a plurality of attitude adjustment trigger switches 1310 which may be arranged along the peripheral side of the end control assembly 210 and configured to control the locking mechanism.

In some embodiments, the plurality of attitude adjustment trigger switches 1310 may be configured to control the locking mechanism. The plurality of attitude adjustment trigger switches 1310 may be electrically connected to the plurality of electromagnets 1321, respectively. The attitude adjustment trigger switches 1310 may control power on and power off of the plurality of electromagnets 1310. The plurality of attitude adjustment trigger switches 1310 may be electrically connected to the robot body 110. Merely by way of example, when the plurality of attitude adjustment trigger switches 1310 are operated, the plurality of attitude adjustment trigger switches 1310 may control the plurality of electromagnets 1321 to be energized, so that the extension shaft controlled by the plurality of electromagnets 1321 may be separated from the end control assembly 210, and the end control assembly 210 may be unlocked to move. When the plurality of attitude adjustment trigger switches 1310 are operated again, the plurality of attitude adjustment trigger switches 1310 may control the plurality of electromagnets 1321 to be de-energized, and the extension shaft of the plurality of electromagnets 1321 may extend to lock the end control assembly 210. Controlling the end control assembly 210 to be locked or unlocked may be realized by energizing or de-energizing the plurality of electromagnets 1321.

In some embodiments, before the attitude adjustment action is performed, the plurality of electromagnets 1321 may be unlocked through the attitude adjustment trigger switches 1310, and the extension shaft of the plurality of electromagnets 1321 may be controlled to retract. In this case, the end control assembly 210 may move to realize the adjustment of the spatial attitude of the end executor 130. When the attitude adjustment trigger switches 1310 are operated again, the extension shaft of the plurality of electromagnets 1321 may be controlled to extend, and the end control assembly 210 cannot move, thereby avoiding falsely triggering the attitude adjustment action when performing operations such as surgery. For example, when the end executor 130 corresponding to the end control assembly 210 is a puncture needle, the puncture needle cannot be rotated during puncturing based on clinical requirements, to ensure the stability of the puncture process and the puncture effect. Therefore, the attitude adjustment action may be performed before the puncture action is performed. After the attitude adjustment action is completed, the end control assembly 210 may be locked by the attitude adjustment trigger switches 1310, and finally the puncture action may be performed. The attitude adjustment action may also be performed alternately with the puncture action, as long as the end control assembly 210 is unlocked before the attitude adjustment action is performed, and the end control assembly 210 is locked before the puncture action is performed.

In some embodiments, the attitude adjustment assembly 220 may further include a plurality of inclination detectors (not shown). The plurality of inclination detectors may be arranged along the peripheral side of the end control assembly 210. The plurality of inclination detectors may be configured to detect an inclination of the end control assembly 210 and transmit the inclination of the end control assembly 210 to the communication device 120. When the end control assembly 210 is inclined towards a certain direction, an inclination detector corresponding to the direction may detect a inclination state of the end control assembly 210, and then detect the inclination of the end control assembly 210. The inclination detectors may be electrically connected to the robot body 110. The inclination detectors may feedback the inclination of the end control assembly 210 to the robot body 110, and the robot body 110 may adjust the spatial attitude of the end executor 130 according to the inclination, so that the end executor 130 may be aligned with the target point.

In some embodiments, when the end control assembly 210 is inclined, the end control assembly 210 may not correspond to any inclination detector, but correspond to a position between two inclination detectors. In this case, the two inclination detectors may jointly detect the inclination of the end control assembly 210. The principle of jointly detecting the inclination of the end control assembly 210 by the two inclination detectors may be substantially the same as the principle of detecting the inclination of the end control assembly 210 by one inclination detector, which may not be repeated herein.

Merely by way of example, there may be four inclination detectors which are evenly distributed along the peripheral side of the end control assembly 210. The end control assembly 210 may realize the adjustment of the spatial attitude of the end executor 130 through the four inclination detectors. That is, when the end control assembly 210 moves toward any inclination detector, the adjustment may be realized through the inclination detector of the direction, and when the end control assembly 210 needs to move in another direction, the end control assembly 210 may move toward another inclination detector.

In some embodiments, an emergency stop switch, a complete machine switch, etc. may also be provided. The emergency stop switch and the complete machine switch may be electrically connected to the robot body 110, respectively. The emergency stop switch may perform an emergency stop operation to prevent the master manipulator being unable to stop the operation in case of an accident. The complete machine switch may be configured to realize an on/off operation of the device.

In some embodiments, a plurality of indicator lamps and corresponding status indication units thereof may also be provided. The plurality of indicator lamps may include, but may not be limited to, a rotation indicator lamp of the end control assembly 210, or the like. The status indication units may be configured to control on/off of each indicator lamp. When the rotation indicator lamp of the end control assembly 210 flashes, the robot body 110 may receive a trigger signal, or the robot body 110 may shield the signal. When the locking mechanism performs unlocking, the state of the plurality of electromagnets 1321 may be detected by the state detection units 1322 and reported to the robot body 110, and a direction of the end control assembly 210 may be identified by the inclination detectors and reported to the robot body 110.

Figure 14:
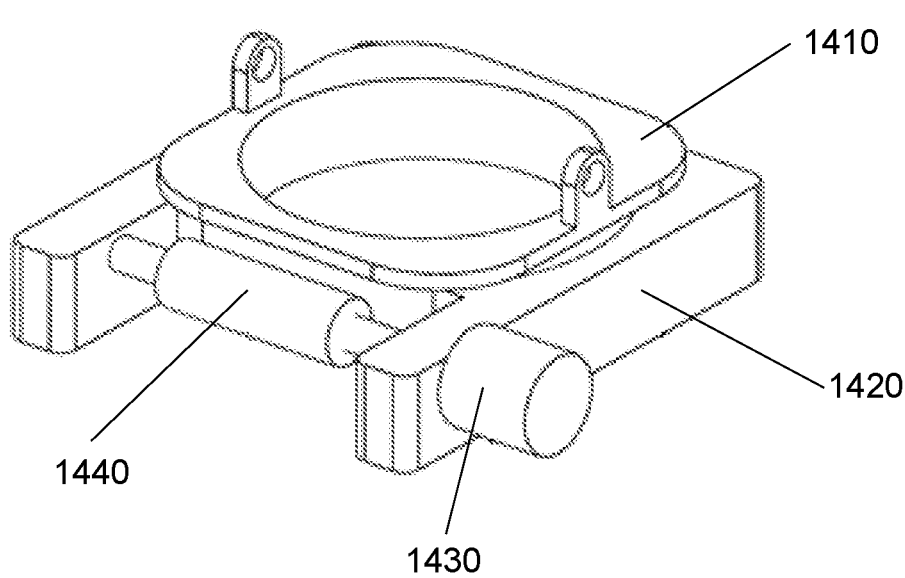
FIG. 14 is a schematic diagram illustrating an exemplary base according to some embodiments of the present disclosure.

FIG. 14 is a schematic diagram illustrating an exemplary base according to some embodiments of the present disclosure. The base 230 in the embodiments of the present disclosure will be described in detail below. It should be noted that the following embodiments are only used to explain the present disclosure, and do not constitute a limitation to the present disclosure.

In some embodiments, the master manipulator 200 (500) may further include the base 230. The base 230 may be disposed on a bottom of the attitude adjustment assembly 220 for supporting and carrying. In some embodiments, the base 230 may be provided with a relatively heavy counterweight, which may not cause the whole device to shake during operation, and the whole device may remain stable. It should be noted that, as a platform for supporting and carrying, the base 230 may be applied to the master manipulator 200, may also be applied to the master manipulator 500, and may further be applied to a device of another structure as a base platform. The base 230 may be described with being applied to the master manipulator 200 as an example merely for illustrating the structure of the base 230, which may not be limited herein.

In some embodiments, the base 230 may be in a shape of a flat plate, which may be convenient for placing the base 230 on a horizontal table for operation. In some embodiments, a middle part of the base 230 may be hollowed out for placing another device. For example, the end control assembly 210 and the attitude adjustment assembly 220 may be arranged in a hollowed-out part in the middle of the base 230 and connected to the base 230. In some embodiments, holes may be provided on the base 230 to facilitate movements of devices flexibly arranged on the base 230. For example, a synchronous wheel rotatably arranged on the base 230 may be rotated to a position below the table of the base 230 through the holes. In some embodiments, the base 230 may be rotatable, to drive the attitude adjustment assembly 220 and the end control assembly 210 disposed thereon to rotate together, to map an attitude adjustment plane where a functional assembly at an end of a robotic arm is located.

In some embodiments, the base 230 may include a base body 1420 and a rotating platform 1410. By setting the rotating platform 1410, the attitude adjustment assembly 220 may add a degree of freedom for mapping the attitude of the robot. This degree of freedom may map the attitude adjustment plane of the end executor 130, so that the master manipulator 200 forms a one-to-one mapping relationship with the robot. As shown in FIG. 14, the rotating platform 1410 may be fixedly connected to a second rotating mechanism of the attitude adjustment assembly 220. The rotating platform 1410 may be rotatably connected to the base body 1420. A rotation plane of the rotating platform 1410 may be parallel, relative to a rotating plane of the base body 1420, to a plane where the base body 1420 is located, and the rotating platform 1410 may be related to a motion of at least one joint of the robot. In some embodiments, the rotation plane of the rotating platform 1410 may not be parallel, relative to the rotating plane of the base body 1420, to the plane where the base body 1420 is located, as long as the mapping relationship between the master manipulator 200 and at least one joint of the robot is guaranteed.

In some embodiments, the base body 1420 may be a frame structure, and a shape of the base body 1420 may be a square, a circle, a polygon, etc., which is not limited here. An installation space may be provided in a middle of the base body 1420, and a dimension of the installation space may correspond to a dimension of the rotating platform 1410. The rotating platform 1410 may be arranged in the installation space of the base body 1420 and rotatably connected to the base body 1420. The attitude adjustment assembly 220 may be arranged on the rotating platform 1410.

In some embodiments, the base 230 may further include a driving member 1430 and a transmission assembly. The driving member 1430 may be a driving member (e.g., a motor) that is compatible with power required by the rotating platform 1410. The driving member 1430 may be directly connected to the rotating platform 1410, and may also be connected to the rotating platform 1410 through the transmission assembly, to drive the rotating platform 1410 to rotate. In some embodiments, the driving member 1430 may communicate with the robot body 110 through the communication device 120.

In some embodiments, the transmission assembly may include a worm 1440 and a worm gear that mesh with each other. The worm 1340 may be connected to an output end of the driving member 1430, and the worm gear may be fixedly connected to the rotating platform 1410. When the driving member 1330 drives the worm 1440 to rotate, the worm gear may rotate correspondingly with the rotation of the worm, and drive the rotating platform 1410 to rotate around a perpendicular line of a plane where the rotating platform is located simultaneously. The rotation of the rotating platform 1410 may adjust an overall attitude orientation of the attitude adjustment assembly 220, i.e., change directions of the first mechanism and the second mechanism simultaneously. However, an angle between the first mechanism and the second mechanism may remain constant, which precisely controls a rotation angle between the rotating platform 1410 and the base 1420.

In some embodiments, the transmission assembly may include a driving wheel and a driven wheel. A synchronous belt may be wound around the driving wheel and the driven wheel. The driving wheel may be connected to an output end of the driving member, and the driven wheel may be fixedly connected to the rotating platform. When the driving member 1430 drives the driving wheel to rotate, the driving wheel may drive the driven wheel to rotate through the synchronous belt, and drive the rotating platform 1410 to rotate around the perpendicular line of the plane where the rotating platform 1410 is located. In some embodiments, the transmission assembly may also be a gear, etc., as long as it can be connected to the driving member 1430 and drive the rotating platform 1410 to rotate.

In some embodiments, the rotating platform 1410 may be provided with a fifth encoder. The fifth encoder may detect the rotation angle of the rotating platform 1410 and transmit the rotation angle of the rotating platform 1410 to the communication device 120. The rotation angle detected by the fifth encoder may be transmitted to the robot body 110 through the communication device 120, and the robot body 110 may control an attitude adjustment plane corresponding to at least one joint of the robot to rotate at a same angle according to the rotation angle, to realize the synchronization of the two rotation angles. In some embodiments, the rotating platform 1410 may be actively synchronized with the attitude adjustment plane where at least one joint of the robot is located.

Figure 15:
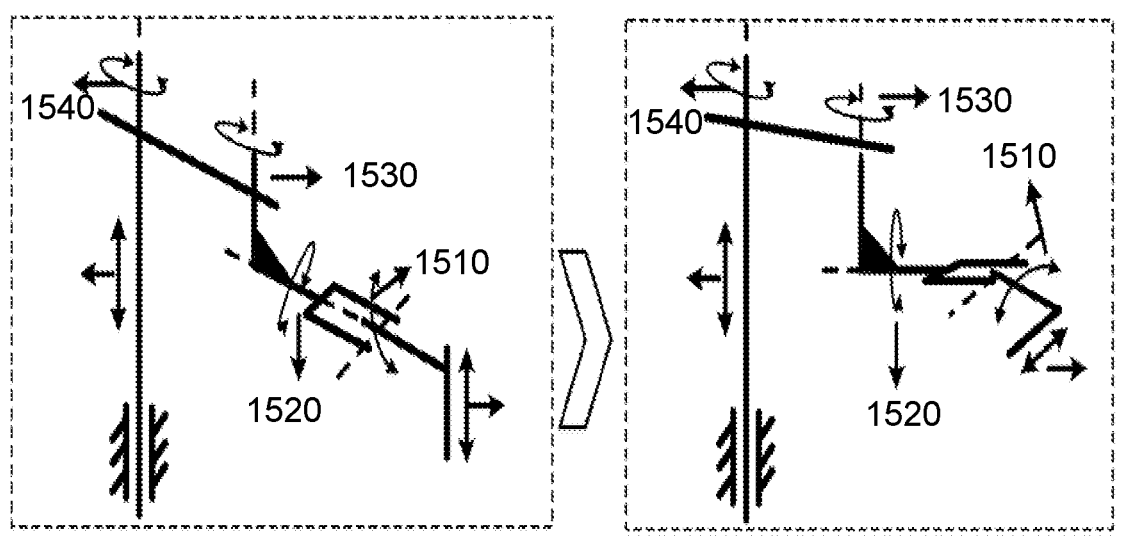
FIG. 15 is a schematic diagram illustrating a principle of performing a multi-degree-of-freedom attitude adjustment by a robot associated with a master manipulator according to some embodiments of the present disclosure.

FIG. 15 is a schematic diagram illustrating a principle of performing a multi-degree-of-freedom attitude adjustment by a robot associated with a master manipulator 200 (500) according to some embodiments of the present disclosure. As shown in FIG. 15, a corresponding relationship between the master manipulator 200 and the attitude adjustment plane where at least one joint of the robot is located may be fed back to the robot body 110. Rotation angles of a first adjustment joint 1530 and a second adjustment joint 1540 may be detected, and vectors of the rotation angles may be superimposed to form rotation angle information to be fed back to the robot body 110. A control command may be transmitted to the driving member 1430 through the communication device 120 based on the rotation angle information, so that the driving member 1430 drives the rotating platform 1410 to rotate by a corresponding angle (a vector sum of the first adjustment joint 1530 and the second adjustment joint 1540), and the mapping of the master manipulator 200 to the attitude adjustment plane of the robot is realized (i.e., the rotation of the rotating platform 1410 with respect to the base 1420 is related to a motion of at least one joint of the robot). The process may be carried out after the attitude adjustment joints of the robot are positioned (the operator may freely adjust the attitude). In this way, the degree of rotational freedom of the rotating platform 1410 with respect to the base body 1420 may be set as an active mapping joint, and the same mapping as the robot attitude may be realized without manual dragging. It should be noted that the application of the base 230 to the master manipulator 500 may also have the same mapping relationship, which may not be repeated herein.

The attitude adjustment plane where the attitude adjustment joints of the robot are located may be realized by the vector sum of the rotations of the first adjustment joint 1530 and the second adjustment joint 1540. The attitude adjustment joints of the end executor 130 may respectively correspond to the first mechanism and the second mechanism. In the preoperative preparation stage, it is necessary to first calibrate the attitude of the robot as shown in the left figure of FIG. 15. In this case, the attitude of the end of the robotic arm of the robot may be perpendicular to the horizontal plane, which may be defined as the zero position. Then, each attitude adjustment joint of the robot (the attitude adjustment joint 1510 corresponds to the first mechanism, and the attitude adjustment joint 1520 corresponds to the second mechanism), the first adjustment joint 1530 and the second adjustment joint 1540 of the robot may be adjusted as required, as shown in the right figure of FIG. 15. The adjustment information is recorded one by one and transmitted to the master manipulator 200. The master manipulator 200 respectively controls the first mechanism, the second mechanism and the base 230 to rotate by the corresponding angle, to realize the synchronization of the attitudes of the joints. When the end of the robotic arm of the robot changes the attitude adjustment plane during the positioning process, because the rotation angles of the first adjustment joint 1530 and the second adjustment joint 1540 are divided into positive and negative (left and right) directions in FIG. 15, the rotation angle of the rotating platform 1410 of the master manipulator 200 may be equal to the vector sum of the first adjustment joint 1530 and the second adjustment joint 1540 of the robot. When the robot adjusts the attitude adjustment joints corresponding to the first mechanism and the second mechanism during the positioning process, the rotation angle information of the corresponding attitude adjustment joints with respect to the zero position may be transmitted to the robot body 110 respectively, and the first mechanism and the second mechanism may be controlled to rotate by the corresponding angle with respect to the zero position. After the positioning of the robot is completed, the master manipulator 200 realizes the one-to-one mapping relationship between the attitude of the end control assembly 210 and the attitude of the end executor 130 through the mapping process, i.e., the end control assembly 210 and end executor 130 are completely synchronized; and then the attitude of the end executor 130 may be fine-adjusted through the master manipulator 200 according to CT imaging. It should be noted that the attitude of the end control assembly 210 may not be completely mapped with the attitude of the end executor 130 in a one-to-one manner, but only a partially incomplete mapping relationship may be realized according to requirements.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of the present disclosure are not necessarily all referring to the same embodiment. Furthermore, the particular features, structures or characteristics may be combined as suitable in one or more embodiments of the present disclosure.

In addition, unless clearly stated in the claims, the sequence of processing elements and sequences described in the present disclosure, the use of counts and letters, or the use of other names are not used to limit the sequence of processes and methods in the present disclosure. While the foregoing disclosure has discussed by way of various examples some embodiments of the invention that are presently believed to be useful, it should be understood that such detail is for illustrative purposes only and that the appended claims are not limited to the disclosed embodiments, but rather, the claims are intended to cover all modifications and equivalent combinations that fall within the spirit and scope of the embodiments of the present disclosure. For example, although the implementation of various components described above may be embodied in a hardware device, it may also be implemented as a software only solution, e.g., an installation on an existing server or mobile device.

In the same way, it should be noted that in order to simplify the expression disclosed in this disclosure and help the understanding of one or more embodiments of the invention, in the foregoing description of the embodiments of the present disclosure, sometimes multiple features are combined into one embodiment, drawings or descriptions thereof. This method of disclosure does not, however, imply that the subject matter of the disclosure requires more features than are recited in the claims. Rather, claimed subject matter may lie in less than all features of a single foregoing disclosed embodiment.

In some embodiments, counts describing the quantity of components and attributes are used. It should be understood that such counts used in the description of the embodiments use the modifiers "about", "approximately" or "substantially" in some examples. Unless otherwise stated, "about", "approximately" or "substantially" indicates that the stated figure allows for a variation of ±20%. Accordingly, in some embodiments, the numerical parameters used in the disclosure and claims are approximations that can vary depending upon the desired characteristics of individual embodiments. In some embodiments, numerical parameters should consider the specified significant digits and adopt the general digit retention method. Although the numerical ranges and parameters used in some embodiments of the present disclosure to confirm the breadth of the range are approximations, in specific embodiments, such numerical values are set as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A master manipulator of a robot, comprising:
an end control assembly; and
an attitude adjustment assembly including a first mechanism and a second mechanism, the first mechanism and the second mechanism being connected to the end control assembly, and the end control assembly controlling the first mechanism and the second mechanism to move through the connection between the first mechanism and end control assembly and the connection between the second mechanism and the end control assembly, wherein the first mechanism and the second mechanism rotate independently around their rotation axes, respectively, so that a rotation of the first mechanism driven by the end control assembly has no effect on the second mechanism, and a rotation of the second mechanism driven by the end control assembly has no effect on the first mechanism.

2. The master manipulator of claim 1, wherein
the first mechanism includes a first rotating transmission bar;
the second mechanism includes a second rotating transmission bar; and
an angle between a rotation axis of the first rotating transmission bar and a rotation axis of the second rotating transmission bar is greater than 10°.

3. The master manipulator of claim 2, wherein
the end control assembly directly applies a force on the first rotating transmission bar and/or the second rotating transmission bar.

4. The master manipulator of claim 3, wherein
the first rotating transmission bar is provided with a first guide hole,
the second rotating transmission bar is provided with a second guide hole, and
the end control assembly passes through the first guide hole and the second guide hole.

5. The master manipulator of claim 4, wherein the end control assembly is rotatably connected to a base.

6. The master manipulator of claim 2, further comprising:
a first feedback assembly configured to apply a first attitude adjustment resistance to the first mechanism based on first feedback information; and
a second feedback assembly configured to apply a second attitude adjustment resistance to the second mechanism based on second feedback information.

7. The master manipulator of claim 6, wherein
an end of the first rotating transmission bar is connected to the first feedback assembly, the first feedback assembly includes a first transmission component and a first feedback motor, and the first feedback motor is connected to the first rotating transmission bar through the first transmission component; and
an end of the second rotating transmission bar is connected to the second feedback assembly, the second feedback assembly includes a second transmission component and a second feedback motor, and the second feedback motor is connected to the second rotating transmission bar through the second transmission component.

8. The master manipulator of claim 7, wherein
the first transmission component includes a first synchronous wheel and a second synchronous wheel, the first synchronous wheel is connected to the first rotating transmission bar, the second synchronous wheel is fixed on an output shaft of the first feedback motor, and the first synchronous wheel and the second synchronous wheel are in transmission connection; and the second transmission component includes a third synchronous wheel and a fourth synchronous wheel, the third synchronous wheel is connected to the second rotating transmission bar, the second synchronous wheel is fixed on an output shaft of the second feedback motor, and the third synchronous wheel and the fourth synchronous wheel are in transmission connection.

9. The master manipulator of claim 8, wherein the first synchronous wheel and the second synchronous wheel are in transmission connection through a first rope, a first tensioning member and a second tensioning member are arranged on a side of the first synchronous wheel along a winding direction of the first rope, and two ends of the first rope are respectively fixed by the first tensioning member and the second tensioning member; and the third synchronous wheel and the fourth synchronous wheel are in transmission connection through a second rope, a third tensioning member and a fourth tensioning member are arranged on a side of the third synchronous wheel along a winding direction of the second rope, and two ends of the second rope are respectively fixed by the third tensioning member and the fourth tensioning member.

10. The master manipulator of claim 1, wherein the first mechanism includes a first rotating shaft and a first connecting part, one end of the first connecting part is connected to the first rotating shaft, and another end of the first connecting part is movably connected to the end control assembly;

the second mechanism includes a second rotating shaft and a second connecting part, one end of the second connecting part is connected to the second rotating shaft, and another end of the second connecting part is movably connected to the end control assembly; and an angle between an axis of the first rotating shaft and an axis of the second rotating shaft is greater than 10°.

11. The master manipulator of claim 10, wherein the first connecting part and the second connecting part circumferentially surround the end control assembly.

12. The master manipulator of claim 10, wherein the first connecting part includes a first connecting straight rod and a first connecting curved rod, one end of the first connecting curved rod is connected to the first rotating shaft, another end of the first connecting curved rod is connected to the first connecting straight rod, and the first connecting straight rod is movably connected to the end control assembly; and the second connecting part includes a second connecting straight rod and a second connecting curved rod, one end of the second connecting curved rod is connected to the second rotating shaft, another end of the second connecting curved rod is connected to the second connecting straight rod, and the second connecting straight rod is movably connected to the end control assembly.

13. The master manipulator of claim 10, wherein the angle between the axis of the first rotating shaft and the axis of the second rotating shaft is greater than 85°.

14. The master manipulator of claim 10, further comprising:

a third feedback component configured to apply a third attitude adjustment resistance to the first mechanism based on third feedback information; and a fourth feedback component configured to apply a fourth attitude adjustment resistance to the second mechanism based on fourth feedback information.

15. The master manipulator of claim 14, wherein:

the first rotating shaft is connected to the third feedback component, the third feedback component includes a third feedback motor and a third transmission component, and the third feedback motor is connected to the first rotating shaft through the third transmission component; and the second rotating shaft is connected to the fourth feedback component, the fourth feedback component includes a fourth feedback motor and a fourth transmission component, and the fourth feedback motor is connected to the second rotating shaft through the fourth transmission component.

16. The master manipulator of claim 15, wherein the third transmission component includes a fifth synchronous wheel and a sixth synchronous wheel, a radius of the fifth synchronous wheel is greater than a radius of the sixth synchronous wheel, the fifth synchronous wheel is connected to the first rotating shaft, the sixth synchronous wheel is fixedly arranged on an output shaft of the third feedback motor, and the fifth synchronous wheel and the sixth synchronous wheel are in transmission connection; and the fourth transmission component includes a seventh synchronous wheel and an eighth synchronous wheel, a radius of the seventh synchronous wheel is greater than a radius of the eighth synchronous wheel, the seventh synchronous wheel is connected to the second rotating shaft, the eighth synchronous wheel is fixedly arranged on an output shaft of the fourth feedback motor, and the seventh synchronous wheel and the eighth synchronous wheel are in transmission connection.

17. The master manipulator of claim 16, wherein the fifth synchronous wheel and the sixth synchronous wheel are in transmission connection through a third rope, and a fifth tensioning member is arranged on a side of the fifth synchronous wheel along a winding direction of the third rope; and the seventh synchronous wheel and the eighth synchronous wheel are in transmission connection through a fourth rope, and a sixth tensioning member is arranged on a side of the seventh synchronous wheel along a winding direction of the fourth rope.

18. The master manipulator of claim 17, wherein a first guide member is arranged on an upper side of the fifth synchronous wheel along the winding direction of the third rope, so that the third rope on the fifth synchronous wheel is wound around the sixth synchronous wheel with a first preset pitch; and a second guide member is arranged on an upper side of the seventh synchronous wheel along the winding direction of the fourth rope, so that the fourth rope on the seventh synchronous wheel is wound around the eighth synchronous wheel with a second preset pitch.

19. The master manipulator of claim 1, wherein the attitude adjustment component further includes a locking mechanism, wherein the locking mechanism includes:

a first brake member, configured to lock or unlock the rotation of the first mechanism; and a second brake member, configured to lock or unlock the rotation of the second mechanism.

20. A robot, comprising:

a robot body, an end executor, and a master manipulator, wherein the master manipulator includes:

an end control assembly; and an attitude adjustment assembly including a first mechanism and a second mechanism, the first mechanism and the second mechanism being connected to the end control assembly, and the end control assembly controlling the first mechanism and the second mechanism to move through the connection between the first mechanism and end control assembly and the connection between the second mechanism and the end control assembly;

the end executor is connected to the robot body, the robot body is electrically connected to a communication device, and the master manipulator is electrically connected to the communication device and the end executor, wherein the first mechanism and the second mechanism rotate independently around their rotation axes, respectively, so that a rotation of the first mechanism driven by the end control assembly has no effect on the second mechanism, and a rotation of the second mechanism driven by the end control assembly has no effect on the first mechanism.

* * * * *